United States Patent [19]
Sahadevan

[11] Patent Number: 5,851,182
[45] Date of Patent: Dec. 22, 1998

[54] MEGAVOLTAGE RADIATION THERAPY MACHINE COMBINED TO DIAGNOSTIC IMAGING DEVICES FOR COST EFFICIENT CONVENTIONAL AND 3D CONFORMAL RADIATION THERAPY WITH ON-LINE ISODOSE PORT AND DIAGNOSTIC RADIOLOGY

[76] Inventor: Velayudhan Sahadevan, 200 Granville Ave., Beckley, W. Va. 25802

[21] Appl. No.: 712,623

[22] Filed: Sep. 11, 1996

[51] Int. Cl.⁶ ..................................................... A61B 5/05
[52] U.S. Cl. ............................... 600/407; 378/63; 378/65
[58] Field of Search ............................ 128/653.1, 653.2; 364/413.13; 378/62, 63, 64, 65; 600/407, 410

[56] References Cited

U.S. PATENT DOCUMENTS

| | | | |
|---|---|---|---|
| 4,365,341 | 12/1982 | Lam | 378/65 |
| 4,633,494 | 12/1986 | Klausz | 378/205 |
| 4,791,934 | 12/1988 | Brunnett | 128/653 |
| 4,905,267 | 2/1990 | Miller et al. | 378/208 |
| 5,117,829 | 6/1992 | Miller et al. | 128/653 |
| 5,490,513 | 2/1996 | Damadian et al. | 128/653.2 |
| 5,537,452 | 7/1996 | Shepherd et al. | 378/65 |

OTHER PUBLICATIONS

Khan, F.M.; The Physics of Radiation Therapy, Second Edition, Megavoltage Therapy, pp. 49–66, 1994.
World Health Organization Conference, Advisory Group Consultation on the Design Requirements for Megavoltage X–ray Machine for Cancer Treatment in Developing Countries, Dec. 1993, publication pending.
Quotation: Varian Oncology Systems, CLINAC 600C Radiotherapy Linear Accelerator, 1993.
Quotation: Philips Medical Systems SL15 Linear Accelerator, 1993.
Quotation: Siemens Oncology Care Systems, Mevatron 6740, 1993.
Quotation: Theratronics, Theratron 1000 Cobalt Unit and accessories, 1993.
Khan, F.M.; Treatment Planning II: Patient Data, Corrections, and Setup, The Physics of Radiation Therapy, Second Edition, pp. 260–314, 1994.
Quotation: Varian Oncology Systems, Ximatron CX. 3 phase 12 inch fluroscopy and Ximatron/CT Opinion, 1993.
Ragan, D.P., et al; Clinical Results of Computerized Tomography–Based Simulation With Laser Marking, Int. J. Radiation Oncology Biol. Phys., vol. 34; pp. 691–695, 1996.
Siemens, TMS Advanced Planning System for Radiation Oncology, 1996.

(List continued on next page.)

*Primary Examiner*—Marvin M. Lateef
*Assistant Examiner*—Eleni Mantis Mercader
*Attorney, Agent, or Firm*—Steptoe & Johnson

[57] ABSTRACT

A patient setup and treatment verification system for radiation therapy having diagnostic imaging devices connected to a room containing a megavoltage radiation therapy machine. The diagnostic rooms and the megavoltage therapy room are connected to each other by openings in the shared secondary wall of the accelerator or through an anteroom to the megavoltage therapy room. Daily patient setup for routine and three-dimensional conformal radiation therapy and on-line treatment port verification with superimposed isodose are done with the patient on a diagnostic-imaging table. The patients are transferred from the diagnostic table to the treatment table without changing the verified treatment position. Sliding or rotating shield or maze walled anteroom are used for radiation protection. A patient setup with multiple diagnostic devices in separate chambers allows rapid turnover of patients in the megavoltage treatment room with patients spending much less time in the treatment room. When the diagnostic device is not in use with the megavoltage therapy machine for radiation therapy of patients in a radiation oncology department, it can be used as a routine diagnostic device for a diagnostic radiology department.

43 Claims, 27 Drawing Sheets

OTHER PUBLICATIONS

Siemens, Virtual Simulation System and Conformal Field Projector for Radiation Oncology, 1996.

GE Advantage SIM, CT Simulation in 3D, GE Medical Systems, 1996.

Kooy, H. M., et al, Treatment Planning for Stereotactic Radiosurgery of Intracranial Lesions, Int. J. Radiation Oncology Biol. Phys., 21: pp. 683–693, 1991.

Tsujii, Hirohiko, et al, The Value of Treatment Planning Using CT and An Immobilizing Shell In Radiotherapy For Paranasal Sinus Carcinomas, Int. J. Radiation Oncology Biol. Phys., 16: pp. 243–249, 1989.

Sibley, G. S., et al., The Treatment of Stage III Nonsmall Cell Lung Cancer Using High Dose Conformal Radiotherapy, Int. J. Radiation Oncology Biol. Phys., 33: pp. 1001–1007, 1995.

Vijayakumar, S., et al, Implementation of Three Dimensional Conformal Radiation Therapy: Prospects, Opportunities, and Challenges, Int. J. Radiation Oncology Biol. Phys., 33: pp. 979–983, 1995.

Rosenman, J., et al, Three–Dimensional Display Techniques in Radiation Therapy Treatment Planning, Int. J. Radiation Oncology Biol. Phys., 16: pp. 263–269, 1989.

Khan, F. M., Radiation Protection, The Physics of Radiation Therapy, Second Edition, pp. 474–503, 1994.

Shleien, B. (Ed), The Health Physics and Radiological Health Handbook, Revised Edition, Exposure and Shielding From External Radiation, pp. 163–218, 1992.

MEGAVOLTAGE RADIATION THERAPY MACHINE COMBINED TO DIAGNOSTIC IMAGING DEVICES FOR COST EFFICIENT CONVENTIONAL AND 3D CONFORMAL RADIATION THERAPY WITH ON-LINE ISODOSE PORT AND DIAGNOSTIC RADIOLOGY

The present day radiation therapy for cancer is delivered mostly by megavoltage machines like the medical accelerators or by cobalt-60 units. Among the medical accelerators, linear accelerators are the most widely used system. A few other medical accelerator systems are also in use. They include the old Van de Graaff generator, the betatron and the microtron. Both the Van de Graaff and the betatron accelerators are technically inferior to cobalt-60 unit and to the widely used linear accelerators (Kahn, F. M., Clinical radiation generators, in The Physics of Radiation Therapy, $2^{nd}$ ed., 49–66,1994).

The cobalt-60 units are relatively cheaper to purchase and to maintain than the medical accelerators. Therefore, cobalt-60 machines are the most widely used treatment machines in countries where the purchase and maintenance costs are of major concern. The lower maintenance cost of the cobalt-60 unit is compensated by the five-year periodic replacement of the cobalt-60 source that is very costly. The other major disadvantages of the cobalt-60 machines include its low energy (1.33 MV), high penumbra, higher skin dose, lower dose rate and the difficulties associated with the source handling. If the source is not replaced by the scheduled time, it can result in very poor treatment. The partially decayed cobalt-60 source is an environmental hazard of greater magnitude. The cost of the environmental cleaning up of a partially decayed and mishandled cobalt-60 source was over 34 million dollars in a single incident. There were many radiation associated tragic deaths including those innocent: children who use to play at the dumping site of the cobalt-60 source. For these reasons, the World Health Organization is attempting to replace the present cobalt-60 units with more efficient medical accelerators (World Health Organization, Advisory Group Consultation on the Design for Megavoltage x-ray Machines for Cancer publication pending).

The much higher cost of the medical accelerators both for its initial purchase and its subsequent maintenance is a greater hindrance in its widespread use especially in those countries with limited resources. A today's standard 6 MV medical linear accelerator with its accessory systems could cost about $700,000 or more (Quotation: Varian Oncology Systems 1993, Philips Medical Systems 1993, Siemens Medical Systems 1993). The cost of an accelerator with 15–20 MV photons and varying energy electrons or a modern medical racetrack microtron could reach several millions. A modern cobalt-60 unit with higher source strength may cost to about $ 250,000 but when the accessories, the table and the cost of the source are all added together, its cost is about over $400,000 (Quotation: Theratronics 1993).

The computed tomography (CT) of the tumor bearing regions obtained with the aid of a diagnostic CT is generally used for treatment planning and dosimetric calculations. (Khan, F. M., Treatment planning II: Data, Corrections, and Setup; in The Physics of Radiation Therapy, $2^{nd}$ ed., 260–314,1994). Since these CT are taken in a different department with a routine diagnostic CT, they are often not reproducible under the treatment conditions of a patient on the radiation therapy machine. This positioning error can cause significant error in radiation dose given to the tumor and to the surrounding normal tissue. In general, fractionated radiation therapy is given as one treatment a day for about 30 to 35 treatments to a patient. The difficulties associated with the day to day identical treatment positioning of a patient on the treatment table as the initial dosimetric planning made with the aid of the initial simulation and the diagnostic CT taken elsewhere increases the cumulative dosimetric error both to the normal and the tumor tissue.

Varying methods for aligning the patient to the intended region of treatment and surgery has been developed but in those methods the patients are positioned on the diagnostic imaging table for the initial planning and days after the planning is completed, attempts are made to reposition the patient on the radiation therapy machine's table in an identical manner as the patient was on the diagnostic imaging table before (Miller, D. W.; Patient alignment system and procedure for radiation treatment; U.S. Pat. No. 5,117,829., 1992; Miller, D. W., Method of assembly and whole body, patient positioning and repositioning support for use in radiation beam therapy systems; U.S. Pat. No. 4,905,267; Klausz, R., Method of controlling the positioning of a patient with respect to an X-ray device and installation for carrying out such method; U.S. Pat. No. 4,633,494). The days later reproducibility of patient's positioning as was on the diagnostic imaging table before is difficult and often can be inaccurate. During the course of several weeks of treatment, the patient's contour can significantly change causing the initial planning and the patient's fitting position in an immobilizing device increasingly inaccurate. In this invention, the patient's treatment setup is daily verified with the diagnostic imaging device and the patient is transported in this verified position from the diagnostic table to the treatment table of the megavoltage treatment machine.

Simulators equipped with CT are available to increase the accuracy of the treatment planning (Kahn, F. M., Treatment simulation; in The Physics of Radiation Therapy, $2^{nd}$ ed., 277,1994). The cost of such a modern simulator will exceed the cost of a medium energy medical linear accelerator. (Varian Ximatron/CT Option, quotation by Varian Oncology Systems; received in 1993) Therefore, the CT equipped simulators are not frequently used in most radiation therapy departments. Another recent advancement in Radiation Oncology is the introduction of the CT-based simulator. In this system, a commercial CT is equipped with computer controlled laser drawing device and creation of digital reconstructed radiographs are used. The laser drawing is used to transfer the CT simulation to the patient for the appropriate patient's skin markings. (Ragan D. P., et. al., Clinical results of computerized tomography-based simulation with laser patient marking; in Int. J. Radiation Oncology Biol. Phys., 34: 691–695,1996; Advanced Planning System for Radiation Oncology, advertisement by Siemens Medical Systems, Inc., received in 1996; Virtual Simulation System and Conformal Field Projector for Radiation Oncology, advertisement by Siemens Medical Systems, Inc., received in 1996; GE Advantage SIM CT Simulation in 3D, advertisement by GE Medical Systems, received in 1996). Again this is very costly. Moreover all these systems cannot reproduce the daily treatment setup on the treatment table as in the case of this invention.

In an effort to minimize the daily patient setup error, weekly port verification films with the patient on the treatment table in treatment position are taken with the high energy beams of the treatment machines (Kahn, F. M., Treatment verification; in Physics of Radiation Therapy, $2^{nd}$ ed., 277–281,1994). Because of the Compton effect of the megavoltage beam the image quality of the port film is poorer than the conventional x-ray films. To make the necessary adjustments, the port film has to be reviewed while the patient is still on the accelerating table and in the treatment position. The time needed to develop each port film taken keeps the patient for longer time on the treatment table. It can be very uncomfortable to the patient. It also reduces the efficient use of the accelerator time. In the process of taking a port film, usually a 0.004–0.007 cGy exposure is made to the intended treatment region and on top of it a wider full field 0.002–0.004 cGy exposure is also made. The second exposure is made to assist the anatomic interpretation of the region of interest. This exposes a wider anatomic region to the high-energy radiation than the intended tumor bearing treatment area. It is not practical to take daily treatment verification films. Therefore, a compromise is made by making the treatment port verification only once a week. The developing electronic portal imaging devices (Lam, W. C.; On-line treatment monitoring for radiation therapy; U.S. Pat. No. 4,365,341,1982; Kahn, F. M., Electronic Portal Imaging, in The Physics of Radiation Therapy, $2^{nd}$ ed. 278–279,1994) are costly and it also does not give the diagnostic x-ray quality images.

Three dimensional localization of the tumor and the critical normal structures used in the CT aided 3D conformal radiation therapy planning for stereotactic radiosurgery (Brunnett, K. J., Computer assisted stereotactic surgery system and method; U.S. Pat. No. 4,791,934,1988; Kooy, H. M., et al., Treatment planning for stereotactic radiosurgery of intra-cranial-leasions; in Int. J. Radiation Oncology Biol. Phys., 21: 683–693,1991) and treatment of the paranasal, (Hirohiko, T., et. al., The value of treatment planning using CT and immobilizing shell in radiotherapy for paranasal sinus carcinomas; in Int. J. Radiation Oncology Biol. Phys. 16: 1989) chest Sibley, G. S., et al. The treatment of stage III non-small cell lung cancer using high dose conformal radiotherapy, in Int. J. Radiation Oncology Biol. Phys., 33: 1001–1007, 1995) and other tumor sites (Vijayakumar, S., et al., Implementation of three dimensional conformal radiation therapy: prospects, opportunities, and challenges; in Int. J. Radiation Oncology Biol. Phys., 33: 979–983,1995) can be improved by pretreatment port verification with a CT and subsequent transport of the patient from the CT table to the accelerator table without changing the patient's positioning. It facilitates reproducible treatment setup as is done with the CT. The rapid increase of the three dimensional conventional radiation therapy (3DCRT) has rendered improved control of tumor growth, long term survival and reduced complication of radiation therapy. The present widely used two-dimensional radiation therapy planning (2D) often underestimates the gross tumor volume and hence the chances for missing part of the tumor in the treatment field or its inadequate dosage. The conventional transverse CT display format is not an ideal display of the anatomic relation to the radiation beam as usually used in a treatment settings. The path of the radiation beam that is not in perpendicular to the axis of the transverse CT slice is difficult to visualize. In the 2D planning the isodose is displayed in multiple CT slices which also makes it difficult to compare the best treatment plan. The conventional transverse CT fails to confirm the continuity of a radioactive seed used in the brachytherapy from one CT slice to the next one. The 3D volume rendering as used in the 3DCRT overcomes these shortcomings of the 2D (Roseman, J. et. al., Three-dimensional display techniques in radiation therapy treatment planning; in Int. J. Radiation Oncology Biol. Phys., 16: 263–269,1989). However when the volume rendering 3DCRT is done with the patient on the CT table at a distant and different setup Diagnostic Radiology Department than the actual treatment delivered with the patient on the treatment table of a Radiation Oncology Department, many of these advantageous of the 3DCRT are lost because of the difficulties associated with the reproducibility of the patient's setups at one department to the other.

The stereotactic radiosurgery of intracranial tumors and vascular malformations needs precise and reproducible volume rendering 3DCRT planning. At a Radiation Oncology Department where many stereotactic radiosurgeries are done, the weekly number of such procedures is limited to about four patients. The low number results for having to wait for access to an accelerator, delay in CT data transfer from the Radiology department to the Radiation Oncology department for treatment planning and the subsequent efforts to set up the patient on the accelerator table identically as the CT images was obtained at the Radiology department's CT. Excluding the waiting time for the access to the accelerator, the present turn-around time for the stereotactic radiosurgery is about four hours (Kooy, H. M., et. al., Treatment planning for stereotactic radiosurgery of intra-cranial lesions; in Int. J. Radiation Oncology Biol. Phys. 21: 683–693, 1991).

This invention overcomes the above difficulties. After the daily on-line isodose superimposed treatment port verification by the diagnostic imaging device, the patient is transported directly from the diagnostic imaging device's table to the megavoltage radiation therapy machine's table. From the CT table the flat table top with the patient is rolled on to an extension table. The extension table with the flat tabletop 15 inserted and the patient is rolled on rails to the connecting accelerator room. The patient is transferred to the accelerator table by rolling the flat tabletop insert with the patient to the accelerator table. In this case, after the setup and verification of a patient's treatment on the diagnostic imaging table, the patient does not change the verified setup for treatment. In contrast to this, the present practice is to hope for identical positioning of the patient using markings made on the skin during the simulation with the x-ray simulator. With the present practice of CT imaging at the Diagnostic Radiology Department and delivery of the radiation therapy at a distant Department of Radiation Oncology, it is difficult to reproduce the initial treatment setup at the Department of Radiation Oncology with its megavoltage radiation therapy machine or by the simulator. Moreover during the course of six weeks conventional radiotherapy, there will be physical changes in a patient to make the initial skin markings more and more inaccurate. The significance of this invention's patient transport from the diagnostic-imaging table to the treatment table directly with the daily on-line treatment port verification to improve the quality of the treatment is obvious.

Radiation therapy is the most cost effective treatment for cancer in most developing countries. When diagnosis of cancer is made too late, the surgical treatment is not successful. Chemotherapy is very expensive and is often not well tolerated. By year 2015, about 9 million new cancer cases are expected per year in the developing countries of the world. There are not many medical accelerators in developing countries. (World Health Organization, Advisory Group Consultation on the Design for Megavoltage x-ray Machines for Cancer Treatment in Developing Countries, 6–10 December 1993, Washington, D.C., publication pending). There is also a great shortage of modern diagnostic devices in the developing countries. This shortage will be even higher in the future if no innovative developments are made. Presently, most patients are treated with antiquated old cobalt-60 machines. This is associated with the prohibitive cost of medical accelerators and the modern diagnostic devices. The need to treat as many patients as possible every day with any available megavoltage machine makes the quality and precision of the treatment to suffer. Therefore, there is an acute need for more cost effective and high quality medical accelerators, diagnostic devices and its ancillary machines for delivery of today's standard diagnostic radiology and radiation therapy in the developing countries. This invention's efficient utilization of a megavoltage machine to treat three to four times the number of patients treated as now and the shared use of diagnostic imaging devices for diagnostic radiology and radiation therapy brings the cost-effective, most modern diagnosis and treatment facilities to the developing countries as well.

The megavoltage radiation therapy machine described in this invention can be any of the presently used megavoltage radiation therapy machines including the accelerators or even a cobalt 60 machine. However the disadvantages of the cobalt 60 machine has been described earlier. Among the accelerators, the medical linear accelerators are the most commonly used ones at the present. In the following descriptions, one should know that the word accelerator is used as synonymous to any megavoltage radiation therapy machines.

Any of the commonly used imaging devices can be used for patient setup and verification. In the following examples, the CT combined accelerator is used as an example, but the CT can be replaced with any other appropriate diagnostic imaging devices. The diagnostic imaging techniques using the magnetic resonance imaging (MRI), ultrasonic tomograms, transverse tomographic x-rays or any other similar imaging devises can also be used in place of the CT. The advantages of the MRI and ultrasonic tomograms include no ionizing radiation is used for imaging. In these cases, instead of the CT, another imaging device is placed in the rooms adjacent to the accelerator. There are both advantages and disadvantages for these other imaging devices. The MRI allows a better imaging of soft tissue but it cannot image bone or calcifications. Additional difficulties associated with MRI are the magnetic interference with the metallic objects and the smaller hole of the MRI scanner. Since the megavoltage room and the MRI rooms in this invention are separated from each other, the interference from the metallic objects used in radiation therapy in the megavoltage room is avoided. The drawings shown in the diagnostic room can either be a CT or an MRI. The image quality of the ultrasonic tomogram is poorer than that of the CT and the MRI, but it is much cheaper. It also provides real time information that is extremely useful in the rapid set up of patients for treatment. Because of its smaller size and the real-time scan capability of the ultrasound, it can also be used as an added device within the accelerator room itself for the rapid treatment setup verification of a patient on the accelerator table. The transverse tomogram have poor contrast and spatial resolution. It can also produce artifacts that could interfere with the dosimetric calculations. (Khan, F. M., Treatment planning II: Data, Corrections, and Setup; in The Physics of Radiation Therapy, $2^{nd}$ ed., 260–314, 1994) The use of the word CT in the following descriptions is synonymous to any of the above commonly used diagnostic devices.

The words CT and accelerator are used as an abbreviation for the various diagnostic devices and the megavoltage radiation therapy machines within the contest of their interrelations described in this invention. The CT and the MRI are the most commonly used diagnostic devices for radiation therapy planning. The linear accelerator is the most commonly used megavoltage radiation therapy machine.

An other major advantage of this invention is the dual usage of the diagnostic device. The diagnostic device (CT) when not in use with the megavoltage radiation therapy machine (accelerator) can be used as stand alone diagnostic CT of a Radiology Department. This enhances the cost-efficiency of this system and the cooperative working environment of the Departments of Diagnostic Radiology and the Radiation Oncology.

SUMMARY OF THE INVENTION

The present invention is a combined cost effective system for diagnostic imaging and radiation therapy. The cost effectiveness of radiation therapy component is achieved by means of reducing the idle time of the accelerator during the usual working hours of the day. It also increases the cost efficiency of the conformal radiation therapy. The cost effectiveness of the imaging component is achieved by its combined use as a diagnostic imaging device in a Department of Radiology and as an accessory device for patient setup and the on line verification of the intended treatment in a Department of Radiation Oncology.

In this invention, any of the commonly used diagnostic imaging devices can be used for the initial patient setup and verification. Such imaging devices include but are not limited to CT, MRI, US, tomographic X-ray, and the nuclear medicine imaging devices such as the SPECT and PET scans.

To achieve this purpose, the invention is provided with an accelerator in the accelerator room that is connected to multiple CT in the adjacent CT rooms. The accelerator room is connected to the CT rooms either by openings in the common wall of the diagnostic rooms and the accelerator room or by means of an ante-room to the accelerator room to which the CT room's doors opens. A patient at a desired treatment position on the diagnostic table in the CT room is moved to the accelerator table in the accelerator room or visa versa through the wall opening or through the ante- room of the accelerator. After the patient's transfer to the desired room, the wall opening or the door to the ante-room is isolated with a radiation protective door of desired material and thickness. With the door closed, both rooms function independently of each other. The patient is treated in the accelerator room while the next patient's setup and its on-line verification proceeds in the CT room. After completion of radiation therapy in the accelerator room, the patient leaves the accelerator room through its common entry and exit door. The patient for desired treatment setup enters the diagnostic room through its common entry and exit door. After the patient's setup is verified in the diagnostic room, the door is opened for the patient's transport to the accelerator room. The patient setup and the desired treatment verification is much more time consuming than the actual delivery of the radiation by the accelerator in the accelerator room. Since multiple CT are connected to the accelerator room, a patient whose setup and treatment verification is completed in any of the multiple CT room is transferred to the accelerator room while other patient's setup and verifications are in progress in other CT rooms. This configuration of accelerator and the CT allows more patients to be treated with a single accelerator. When the CT is not in this combined use with the accelerator for radiation therapy of cancer patients of the Radiation Oncology Department, it is used for the routine diagnostic studies of patients of the Diagnostic Radiology Department.

Another object of this invention is the provision of a patient transport mechanism from the CT room to the accelerator room without changes in the verified patient's treatment setup position by the diagnostic device. It is being done by aligning and latching together the diagnostic table with an extension table or the accelerator table and transferring the flat table top insert with the patient from one table to the other by rolling it to the accelerator table.

A further object of this invention is the provision of both manually controlled and motor driven radiation protective shutter for opening and closing of the wall opening. With the shutter closed, the accelerator and the diagnostic device can function independently of each other. With an open shutter, the patients is transferred from one room to the other. The facility safety interlocks of the accelerator and the diagnostic device's control console is connected to the shutter to assure safety from the scattered radiation. If the shutter is not fully closed, a warning red light will come up and the machines will not operate to produce radiation.

A still further object of this invention is the provision of maze wall arranged accelerator room to reduce the radiation energy that reaches the wall openings for the connection with the diagnostic device. In this instance the shielding requirement for these openings is treated like that for the accelerator door where multiply scattered radiation with much reduced energy is encountered. With maze walls, the accelerator room is configured with an ante-room in front of it. Patients are transported from the CT room to the accelerator's ante-room space first and then to the accelerator table by means of connecting tables.

A still further object of this invention is the increased accelerator usage by separating the more time consuming patient setup for treatment and treatment portal verifications from the accelerator.

A further object of this invention is the daily on-line pre-treatment verification of the previously planned treatment by daily single or multiple slice check CT with superimposed isodose treatment plan for conventional radiation therapy and for 3DCRT.

Another object of this invention is the provision of an alternate configuration with multiple accelerators combined to the CT to allow both the routine radiation therapy and special purpose radiation therapy such as the stereotactic radiosurgery.

One other object of this invention is the provision of CT-simulation of a patient for radiation therapy with a diagnostic imaging CT that is connected to the accelerator in a manner as to allow the patient transport from the CT table to the accelerator table without any changes in the patient setup done by the CT.

Another major object of this invention is the use of the CT in combination with the accelerator for radiation therapy by the Radiation Oncology Department and as the diagnostic device for diagnostic imaging by the Diagnostic Radiology Department.

BRIEF DESCRIPTION OF THE DRAWINGS

Other objects and advantages of this invention will become more apparent from the specification taken in conjunction with the accompanying drawings, in which.

DETAILED DESCRIPTION OF THE INVENTION

Figure 1:
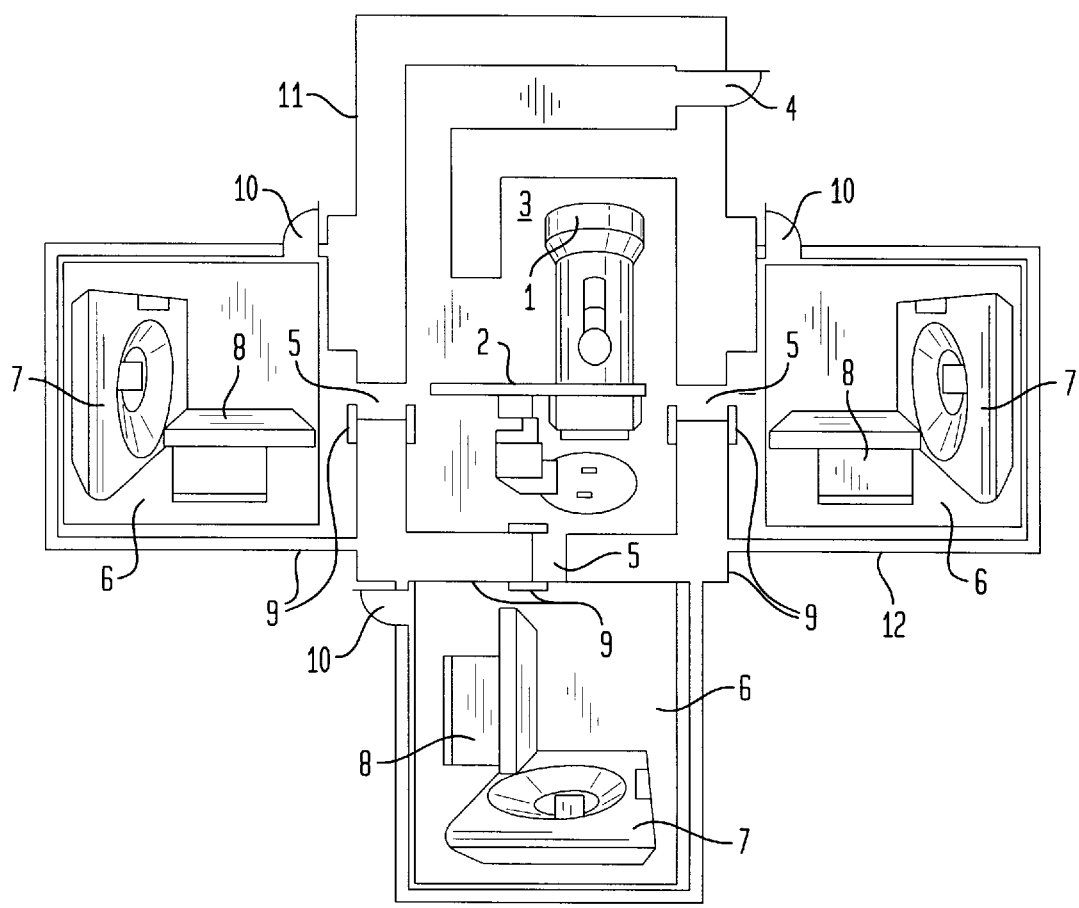
FIG. 1 is a view of the centrally located accelerator connected to three CT, through the wall openings with the shutter moved to the side of the wall at both sides of the rooms.

Referring to the drawing shown in FIG. 1, numeral 1 designates a commercially available medical accelerator and its treatment table 2. It is housed in the accelerator room 3 which is constructed with required thickness radiation shielding material. The accelerator room has its entrance door 4, and wall openings 5, through which it is connected to the adjacent CT rooms 6, each containing a commercially available CT 7, and its table 8. The connecting wall openings between the accelerator room and the CT rooms are opened and closed with sliding shield doors 9. Both sides of the wall openings are fitted with sliding shield doors 9. These sliding shield doors are made of required thickness radiation protective material of a suitable kind. Doors 10 are for entrance to and exit from the CT rooms. The accelerator room's shielding walls 11 and the CT room's shielding walls 12 are constructed with the appropriate thickness shielding material based upon the photon beam's energy. Since the accelerator's photon beam is in the range of MeV and the CT's photon beam is in the range of KeV, the accelerator's walls 11 have much higher wall thickness than the CT room's walls 12.

Figure 2A:
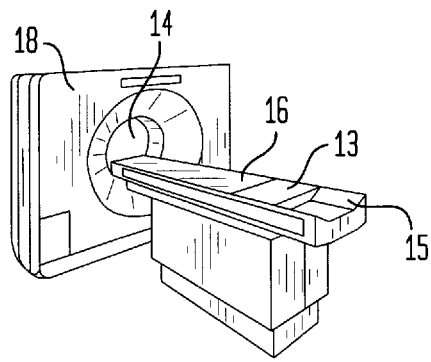
FIGS. 2A–C show the sectional views of a modified commercially available CT table for patient transport through the wall opening and the closed wall after the patient has been transferred from one room to the other.
Figure 2B:
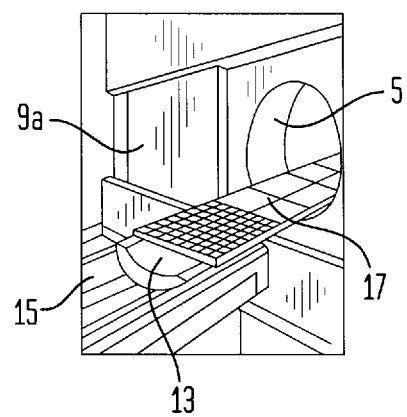
Figure 2C:
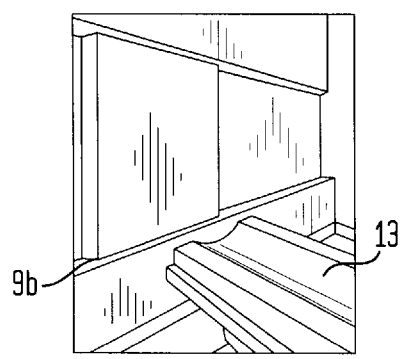
Figure 3A:
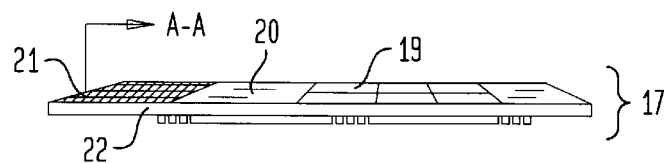
FIGS. 3A–D show sectional and cross sectional views of a modified CT table.
Figure 3B:
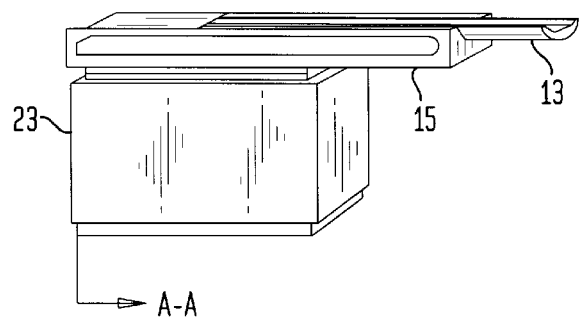
Figure 3C:
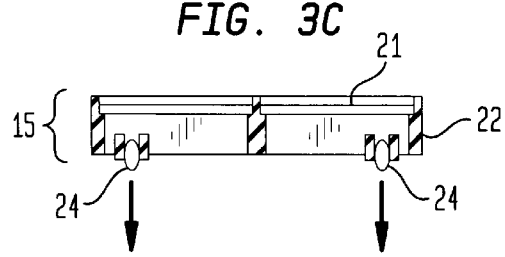
Figure 3D:
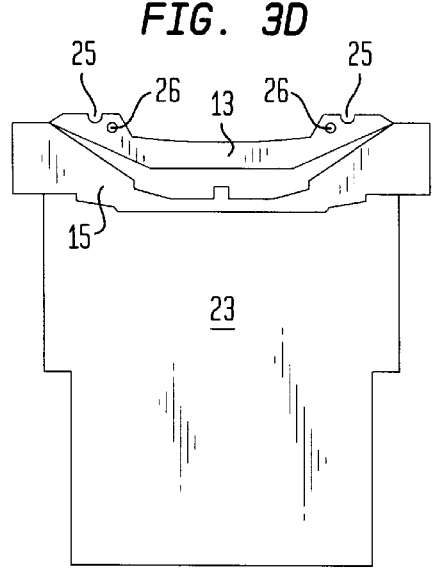

In FIGS. 2A–C, a commercially available CT's integration for its use with the accelerator is shown. FIG. 2A shows a commercially available CT as it relates to this invention. The CT table's cradle 13 moves forward towards the gantry's central opening 14, and backward on its intermediate support 15. Commonly a flat table top insert 16 for placement of a patient on a flat surface on top of the CT table's cradle 13, for radiation therapy planning CT scans is used to reproduce the same outlines of a patient's body contour as the one that would result when the patient is placed on the flat table top of an accelerator table. According to this invention, the table top insert 16 is modified to be identical to the table top 17 of an accelerator table and for use as a common table top for the accelerator and the CT tables. A gantry 18 with a central opening 14 having a diameter of about 70 cm is generally used for a radiation therapy planning CT. The opening accommodates both the patient and the devices used for the patient's settings for radiation therapy. As shown generally in FIG. 2B and 2C are the opened and closed wall openings. FIG. 2B shows the modified table top insert 17 extended through the center wall opening 5 towards the accelerator room. FIG. 2C shows the closed wall opening without the table top insert 17 on the CT table's cradle 13 to indicate the modified table top 17 has completely moved to the accelerator room. In FIG. 2B, the opened wall opening 5 with the table top insert 17 extended through it is shown. The shield door 9 is slid away from the wall opening 5 and is brought to its open position 9a. The forward movement of the CT cradle 13 along with the table top insert 17 and the stationary CT table's intermediate support are also shown in FIG. 2B. After completion of the passage of the table top insert 17 from the CT room to the accelerator room through the wall opening 5, the sliding shield door 9 is slid to its closed position 9b as shown in FIG. 2C. The CT table's cradle 13 is retracted and is brought to rest on the CT table's intermediate support 15 as illustrated in FIG. 2C.

In FIG. 3, the sectional view of the CT table with the modified flat table top insert 17 and the CT table's cradle 13 and intermediate support 15, with their cross sectional view through plane A—A is shown. FIG. 3A shows the modified table top insert. Similar to a commercial accelerator's table top, the modified table top insert 17 has portions for mylar insert 19, a wood top 20, a tennis racket opening 21 and its non-metallic frame 22. The cross-section through plane A—A is further illustrated in FIG. 3C. In FIG. 3B, a commercial CT table and its association with the modified table top insert 17 is illustrated. The table top insert 17 is made to fit on the CT table's cradle 13 and to roll on it. The table top insert 17, the cradle 13 and the intermediate support 15 rest on the top of the table elevator and base assembly 23. The cross section through line A—A is further illustrated in FIG. 3C wherein the cross sectional view of the modified table top insert 17, through line A—A of FIG. 3A is shown. The bottom of the modified table top's frame 22 is fitted with two sets of rollers 24 for its guided movements on the CT table and the accelerator tables. The section through the tennis racket 21 of the modified table top insert 17 is also shown. In FIG. 3D, the modifications made to the commercial CT table's cradle 13 through plane A—A as illustrated in FIG. 3B are demonstrated. Both lateral top surfaces of the cradle 13 are modified by forming longitudinal non-metallic guide grooves 25 on which the rollers 24 of the modified table top insert 17 can travel. The fitting of the longitudinal guide grooves within the cradle is further illustrated in FIG. 5,6,7 and 8. At the end of the CT table's cradle 13 two female notches 26 are fitted for connection with the extension table. The guide grooves 25 and the female notches 26 of the cradle, the intermediate support 15, and the elevator and base assembly of the CT table 23 are shown in the cross sectional view of the CT table at A—A plane of the FIG. 3B.

Figure 4A:
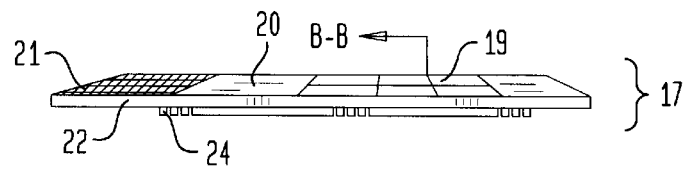
FIGS. 4A and B illustrate the sectional and cross sectional views of a modified accelerator table.
Figure 4B:
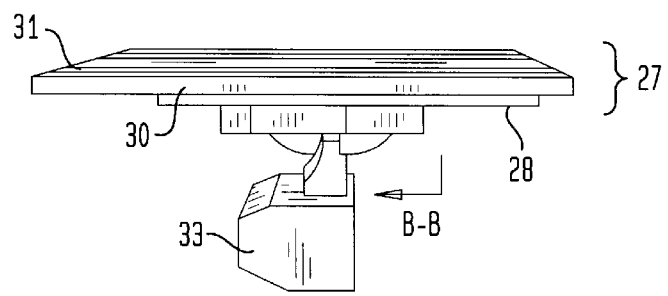
Figure 4C:
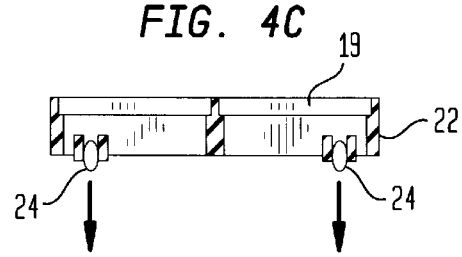
Figure 4D:
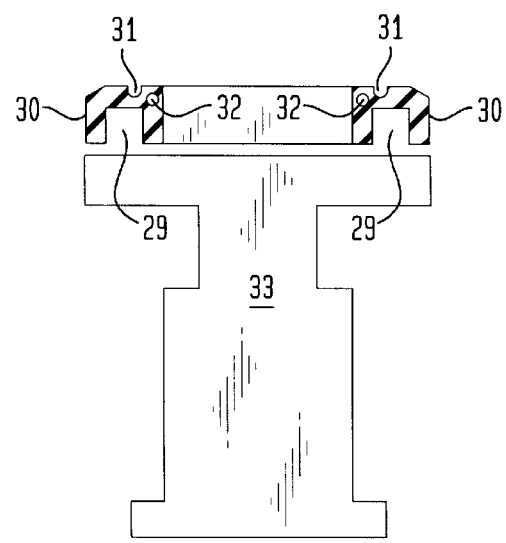

FIG. 4B illustrates the sectional view of the modified flat table top insert 17 with a modified accelerator table and their cross section through the plane B—B of FIG. 4A. In FIG. 4A, the accelerator table's top most portion where the patient is placed for treatment is removed and replaced with the traveling modified table top insert 17 which has the identical structural components as the usual accelerator table top, such as the mylar 19, wood 20, tennis racket 21, and the non-metallic frame 22, but it is also fitted with rollers 24 underneath it for its travel from the CT table to the accelerator table and visa versa. Beneath the table top insert 17 is shown a commercial accelerator table. Like the CT table, the commercial accelerator table also has a cradle 27 and an intermediate support 28, but with a slightly different configuration. After removing the commercial accelerator table top's mylar wood and tennis racket, its two side rails 29 (FIG. 4B) are exposed and on which two frames 30 with side grooves 31 are fitted for the travel of the rollers 24 of the modified table top insert 17. The grooves on this frame and those fitted on to the CT table's cradle are aligned to make it a continuous path for the smooth travel of the rollers 24 of the modified table top insert 17 as shown in FIG. 8. At the rear end of the accelerator table's cradle two male notches 32 are fitted interconnectingly with female notches 26 (FIG. 3D at the rear end of the CT table's cradle 13. The accelerator table's cradle 27 and the intermediate support 28 rest on its elevator and base assembly 33.

The cross sectional views at plane B—B through the modified table top insertion 17, accelerator cradle 27, intermediate support 28, and the elevator and base assembly 33 are shown in FIG. 4A. In the cross sectional view as in FIG. 4B the modified table top insert 17, with its frame 22, the mylar 19, and its rollers 24 as aligned to the grooves 31 (FIG. 4A) of the accelerator frame 30 (FIG. 4B) are illustrated through the plane B—B of FIG. 4A. In FIG. 4B the cross sectional view through the plane B—B of the accelerator table is illustrated. The side rails 29 of the accelerator table's cradle 27 are fitted to a frame 30 with side grooves 31 for travel of the rollers 24 of the modified table top insert 17. The male notch 32 on the frames 30 for connection with the female notches 26 of the CT cradle 13 (FIG. 4A) and the accelerator table's elevator and base assembly 33 are also shown. As described earlier, the frames 30 are fitted to the accelerator's table top after removal of its wood 20, mylar 19, and the tennis racket 21, (FIG. 4A).

Figure 5A:
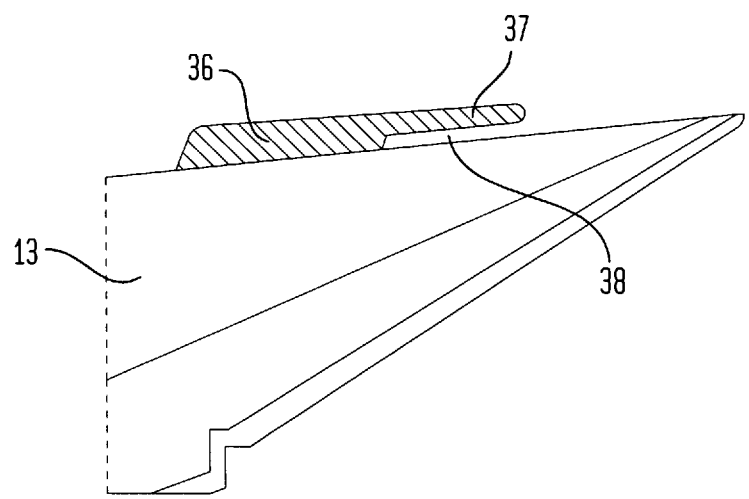
FIGS. 5A–D demonstrate the sectional views of attachment of track and grooves to the section B of the CT transport system for movement of patient on modified table top insert.
Figure 5B:
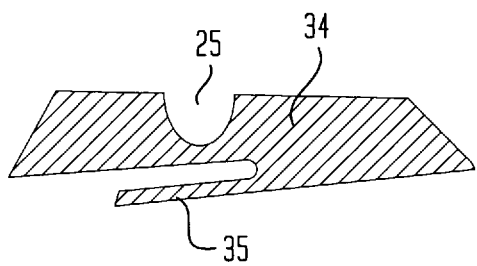
Figure 5C:
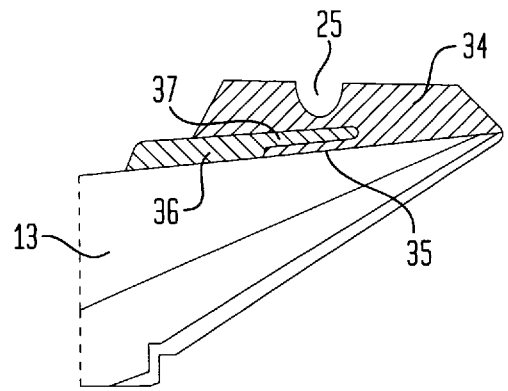
Figure 5D:
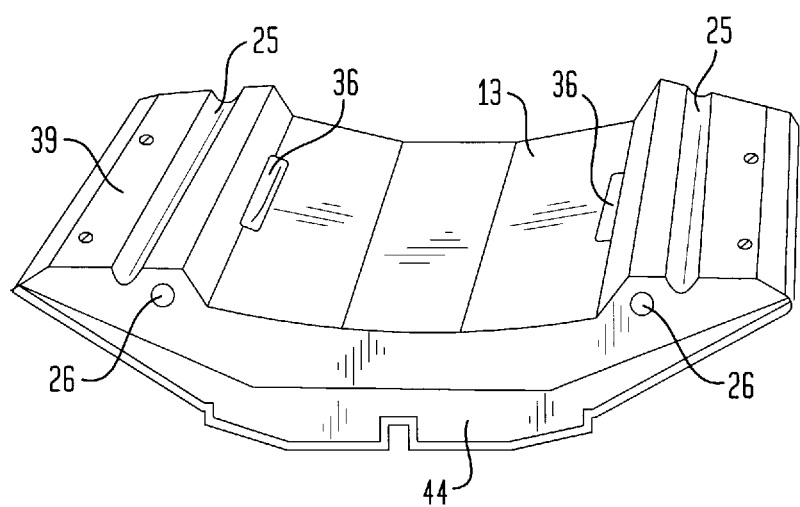

The sectional drawings in FIG. 5A–D show the prefabricated track insert 34 and flange 35 with grooves 25 for the modified flat table top insert's 17 rollers 24 to travel on the CT table's cradle 13, its fitting to the cradle's existing fastener site 36, and the continuous grooves 25 on CT table's cradle 13. In FIG. 5A, the existing fastener site 36 and its wedge like flange 37 on the CT table's cradle 13 is generally used to insert fasteners to its slot 38 for the secure positioning of a patient on the cradle. The fastener is attached to the hollow under surface created by the wedge like flange 37 of the fastener site. The modification introduced to this existing fastener is shown in FIGS. 5B, C and D. In FIG. 5B, the slot 38 is made to accept a similar but reversed flange 35 from a prefabricated track insert 34. The arrow indicates the direction by which the prefabricated track insert 34 is fitted to the existing fastener site 36 of the CT table's cradle 13. In FIG. 5C the completed assembly of the prefabricated track insert 34 with the preexisting fastener site 36 at the CT table's cradle is shown. The reversed flange 35 of the prefabricated track insert is brought underneath the flange 37 of the CT cradle's existing fastener site 36 and is firmly fitted together. Fastening of a longitudinal prefabricated track insert to the CT cradle's existing longitudinal fastener site 36 creates a continuous groove 25 on top of the CT cradle. (See also FIG. 6.) A pair of continuous grooves 25 secured with screws 39 onto the CT cradle's lateral elevations are illustrated in FIG. 5D. The female notches 26 at the end of the CT cradle for connection with the table extension are also shown here. The CT cradle's rear end 44 and its relation with other connecting tables to make a continuous connection from the CT table to the accelerator table are best shown in FIG. 7.

Figure 6:
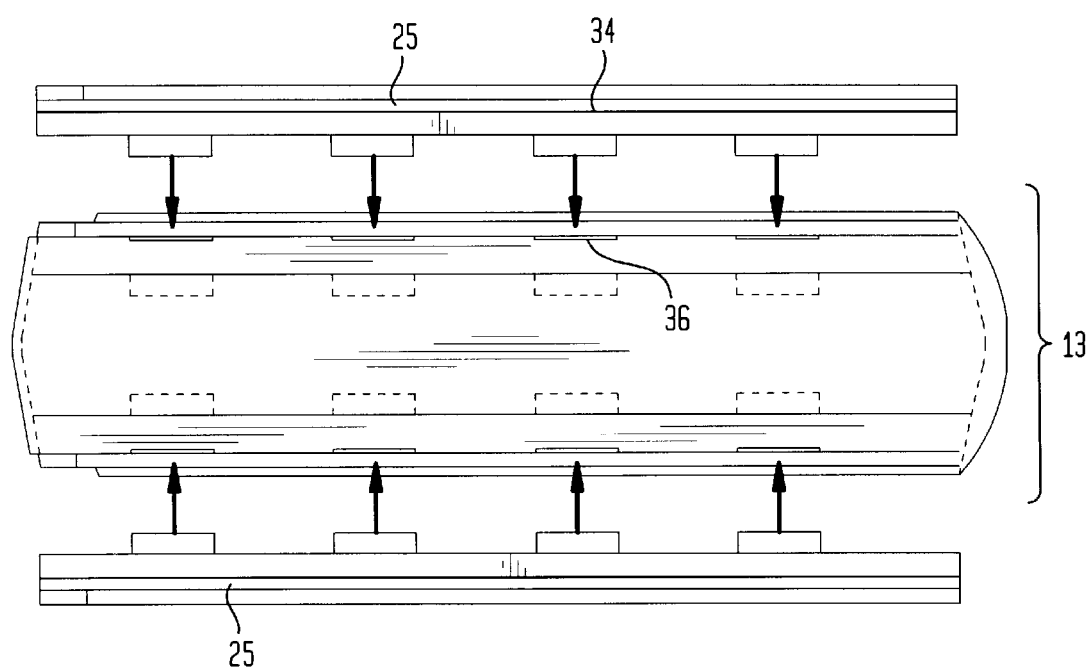
FIG. 6 shows the top view of the section B of the CT transport system after removing the table top insert D. The guide rail insert is aligned for insertion and fastening to the section B's existing lateral side slots.

FIG. 6 shows a top longitudinal view of the CT table's cradle 13 with its existing fastener sites 36 on both of its lateral sides. The modified flat table top insert 17 which sits on top of the cradle is removed to illustrate this longitudinal top view of the CT table's cradle. The arrows on both sides of the cradle indicate the longitudinal prefabricated track insert 34 as aligned for insertion into its existing fastener site's slots 36 to establish the continuous longitudinal grooves 25 on top of the CT cradle for the modified flat table top inserts 17 rollers 24, forward and backward. The configuration of these grooves 25 on top of the CT cradle 13 is further illustrated in the sectional drawing at the bottom of the FIG. 5.

Figure 7:
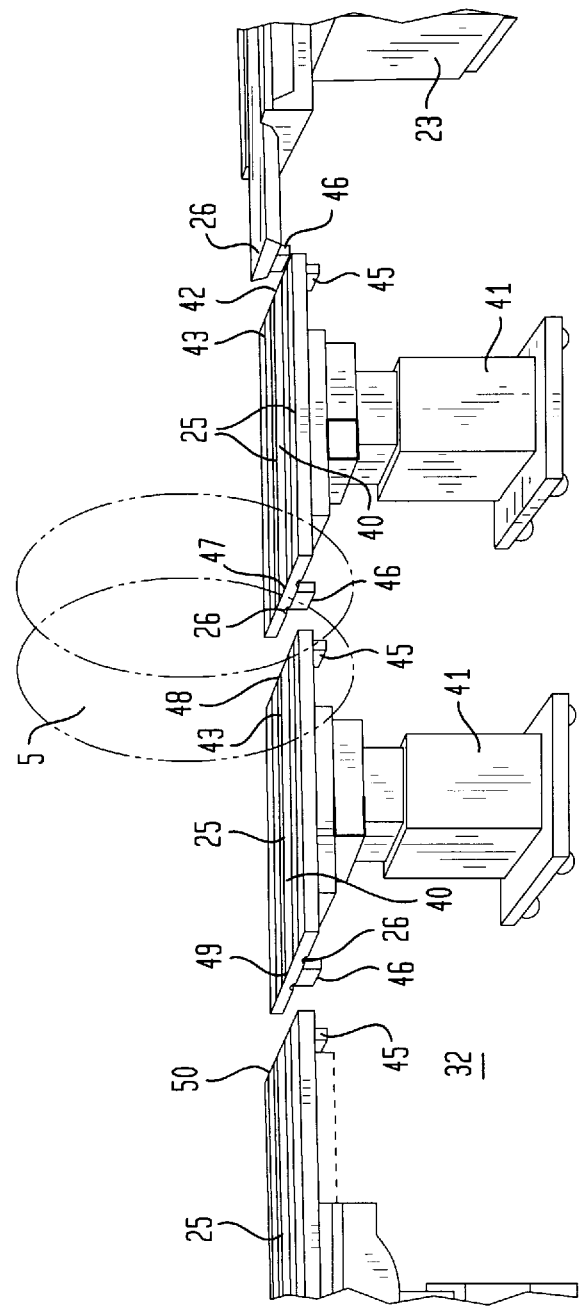
FIG. 7 illustrates a table top extension that is fixed on to a small table which can be rolled in place for alignment and fastening to the CT table. The other end of this table top extension can be connected the corresponding end of a similar table top extension from the accelerator room and brought in alignment with each other through the wall opening.

FIG. 7 illustrates a table top extension 40 on top of an extension table 41 placed in the CT room as a means to create an extension of the CT table towards the accelerator room through the wall opening. Its forward end 42 is fitted with two male notches 43 which are identical to the accelerator table's cradle end's male notches 32 (FIG. 4 and 8). It connects with the corresponding female notches 26 at the rearward longitudinal end 44 of the CT cradle. These connecting notches are brought in alignment and fastened with the female notches 26 at the rearward end 44 of the CT table's cradle. Both table ends are further firmly attached with a latching clip 45 at the under surface of the table extension and with the clip fastener 46 at the CT cradle's under surface. The other end 47 of this table extension can reach the center of the wall opening 5. This end 47 of the table extension is fitted with two female notches 26 and a clip fastener 46 which are identical to those at the CT cradle's connecting end 44. This end 47 can be connected to the two male notches 43 from the rearward end 48 of an extension table from the accelerator room. These male notches are identical to the male notches 43 of the extension table in the CT room and the accelerator cradle's rearward end's male notches. All these male notches are identified by the numeral 43. After the connection with the rearward end of the extension table from the accelerator room 48 with the rearward end of the extension table from the CT room 47 they are firmly fastened with a latching clip 45, at the rearward end of the extension table from the accelerator room and by the clip fastener 46 at the rearward end of the extension table from the CT room. The latching clips 45 and the clip fasteners 46 are identical for the extension tables, accelerator cradle's end and the CT tables cradle end, and hence they are identified by the same numeral 45 for the latching clip and 46 for the clip fastener. Both table top extensions are brought to the center of the wall opening 5 for this firm connection with each other. The opposite end 49 of the table extension from the accelerator room facing the cradle end of the accelerator table with its female notches 26 and the clip fastener 46 is similarly connected with the rearward end 50 of the accelerator table's cradle by attaching the accelerator table end's male notches 32 with the female notches 26 of the extension table's end 49 and fastening them together with the latching clip 45 and the clip fastener 46. The projecting male notches 32 and 43 of the table ends 50 and 42 are slid back when tables are not connected and pushed forward when these table end's connections are needed. These connections and the fastening of the extension table from the CT room with the CT cradle on one side and with the extension table from the accelerator room with the extension table from the CT room through the wall opening and its final connection with the accelerator table's cradle end in the accelerator room on the other side provides the continuity of the table from the CT table's cradle to the accelerator table's cradle. This facilitates the establishment of the continuous grooves 25 from the CT cradle 13 in the CT room to the accelerator cradle 27 in the accelerator room (FIG. 8). The flat table top extension 17 can be rolled towards the accelerator room or to the CT room over these continuous longitudinal grooves 25 which are now connected with the CT cradle and to the accelerator cradle through the wall opening (FIG. 9 and 10). After a patient on the modified flat table top insert 17 is rolled from the CT cradle in the CT room to the accelerator cradle in the accelerator room through the wall opening 5, the extension tables are disconnected from each other and from the CT cradle and the accelerator cradle, and they are moved away from the wall opening. The sliding shield door 9 at the side of the accelerator room and the other sliding shield door at the side of the CT room are moved to close the wall opening from both sides as in FIG.2.

Figure 8A:
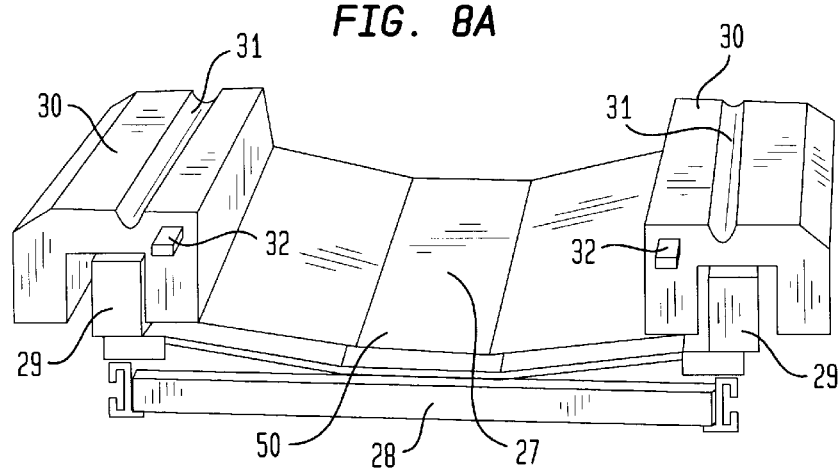
FIGS. 8A–C illustrate the modifications made to the rearward end of the accelerator table's section F and to the CT table's section B to accommodate these two table's connections with each other. The sectional view of the two tables connected together is also shown.
Figure 8B:
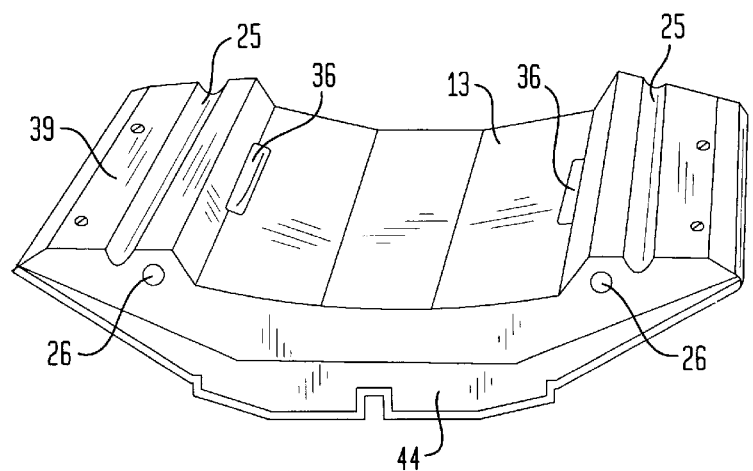
Figure 8C:
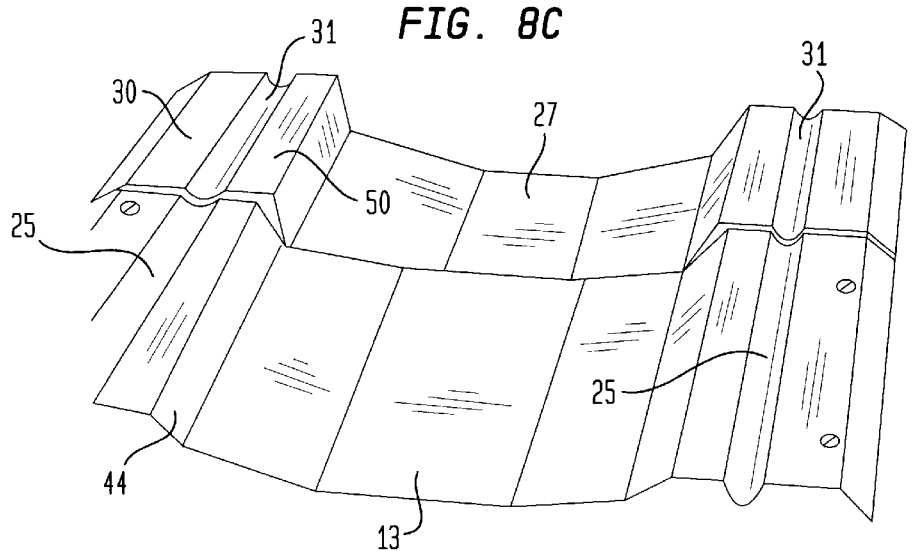

FIGS. 8A–C are an illustration of the modifications to a commercially available accelerator table's cradle's rearward end's 50 for its connection with either an extension table's female notches 26 or with the CT cradle's rearward end 44. FIG. 8A is an illustration of the modifications made to the accelerator table end 50. It is fitted with two frames 30 on top of its each side rails 29 of the accelerator table's cradle 27. These frames contain grooves 31 which are symmetrical to the CT table's prefabricated track insert's groove 25 (FIG. 5B and 8B). The modified flat table top insert 17 travels on the grooves 25 of the CT table's cradle 13 and on the grooves 31 of the accelerator table's cradle 27. Symmetry of these grooves enables the flat table top insert 17 to travel on top of both these tables smoothly. The sectional view of the CT cradle's rearward end 44 with the prefabricated track 25 firmly attached to it is also shown in FIG. 8B. Its side by side illustration with the accelerator cradle's modified rearward end 50 is to demonstrate their connections to each other as shown in FIG. 8C Alternatively, these table ends can also be connected to the connecting ends of an extension table (FIG. 7). In this illustration, the modified accelerator cradle's 27 end 50 with the male connectors 32 (FIG. 8A) is attached to the CT cradle's 13 female notches 26 at the CT table's end 44 (FIG. 8B). These table ends are firmly fastened together with latching clip 45 and clip fastener 46, (FIG.7). After these connections, the accelerator table's side grooves 31 on its frame 30 become a continuous groove with the CT cradle's side grooves 25.

Figure 9A:
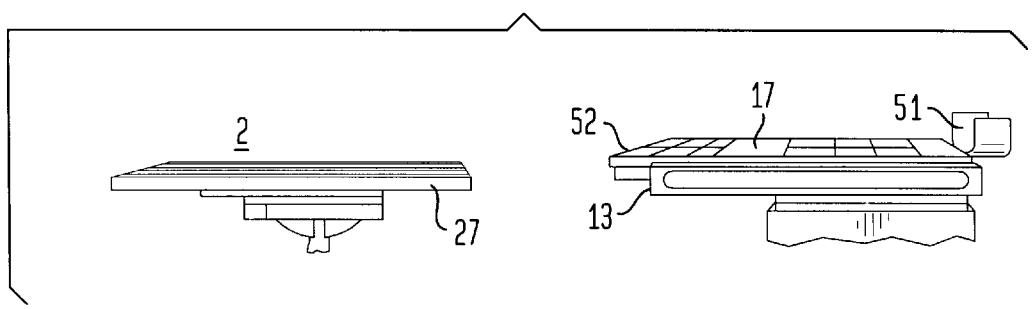
FIGS. 9A–C demonstrate the transport of the modified flat table top insert of the CT table section D and thereby also the patient from the CT table to the accelerator table through the wall opening.
Figure 9B:
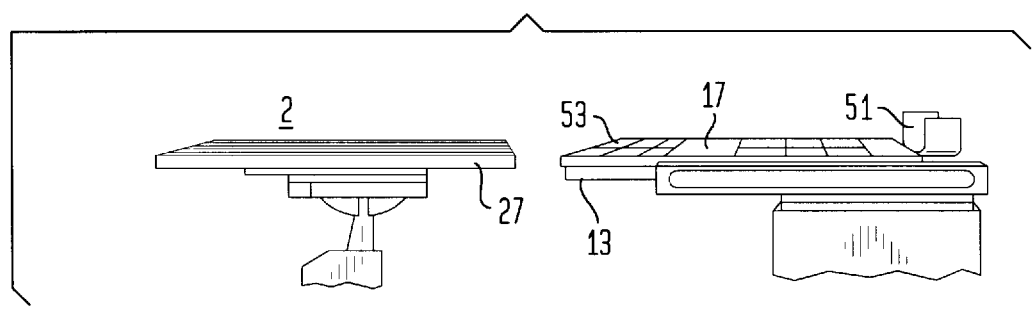
Figure 9C:
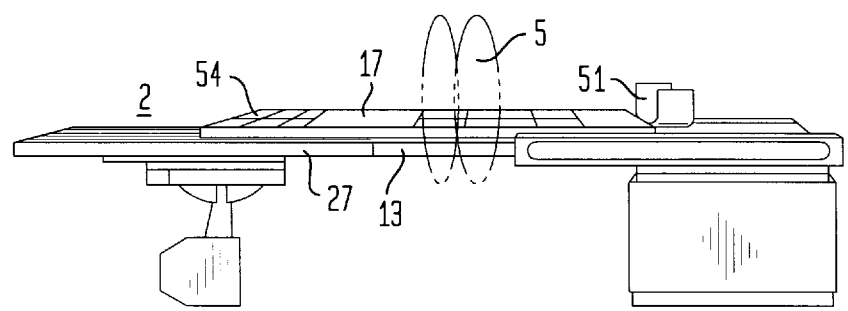

In FIGS. 9A–C the patient transport from the CT table in the CT room to the accelerator table in the accelerator table is illustrated. The modified flat table top insert 17 is fitted with a head holder 51 and rests on the CT cradle 13 in position 52, in FIG. 9A It is slightly advanced towards the wall opening and the accelerator table 2. For illustration purposes, this initial position is indicated as 52 in FIG. 9A. In FIG. 9B the flat table top insert on CT cradle is rolled further towards the wall opening and the accelerator table 2 and brought to position 53. This continuous forward advancement of the modified flat table top insert towards the wall opening 5 and the accelerator table 2 is further illustrated in FIG. 9C. The flat table top insert passes through the wall opening 5 reaching the accelerator table by its forward advancement over the accelerator table's cradle 27. It is thus brought to about the half way point over the accelerator cradle in position 54.

Figure 10A:
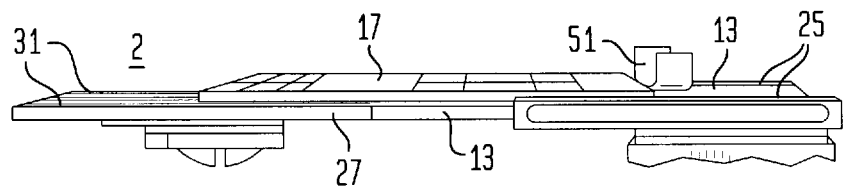
FIGS. 10A–C show the rotation of the accelerator table after the modified CT table top insert, section D has been transferred on top of it to 180 degree to bring the patient's upper body and the head under the accelerator's treatment head in one configuration of the CT and the accelerator placements in their respective rooms.
Figure 10B:
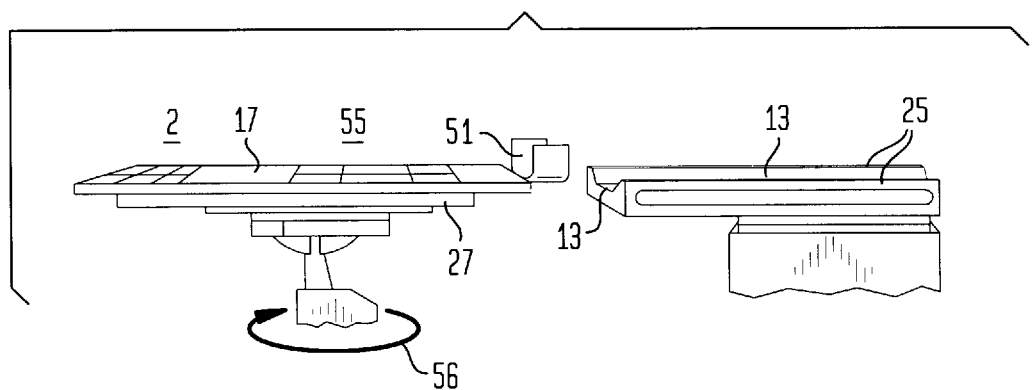
Figure 10C:
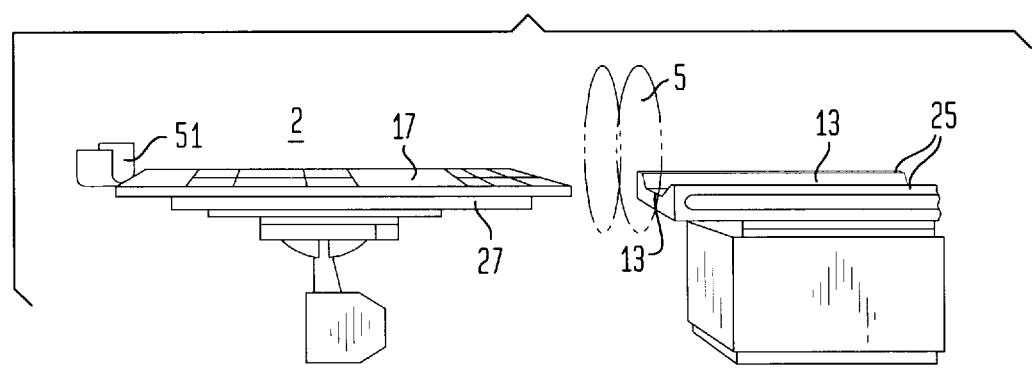

FIGS. 10–C demonstrates the continuous forward advancement of the flat table top insert 17 over the accelerator table's cradle on the grooves 25 of the CT cradle and 31 of the accelerator cradle as in FIG. 10A and FIG. 10B. In FIG. 10B the flat table top insert is transferred completely to the accelerator table 55. Afterwards a 180 degree accelerator table rotation is made to bring a patient's upper body portion with the head holder 51 directly under the accelerator's treatment head when this region is to be treated, see FIG. 10B The arrow 56 indicates the 180 degree rotation of the accelerator table. After the 180 degree rotation of the accelerator table, the head holder 51 is brought to the opposite end of the accelerator table as shown in FIG. 10C. in this bottom drawings. The wall opening and the CT in the opposite CT room is also shown. FIGS. 9A–C and 10A–C thus show a patient's continuous transport form the CT table to the accelerator table and the subsequent rotation of the accelerator table to bring the patient to the desired treatment position without altering the patient's position. In between the CT table and the accelerator table, the extension tables are placed as needed as shown in FIG. 7. In these descriptions the movements of the flat table top insert 17 on the grooves of the CT cradle 13, extension tables 41, and on the accelerator cradle 27 correlate to the transport of a patient on top of the flat table top insert 17. For patients whose setup and verifications were done with the CT placed at 90 and 270 degree angles to the accelerator, only a 90 degree rotation of the accelerator table is required to bring the patient under the accelerator's treatment head.

Figure 11A:
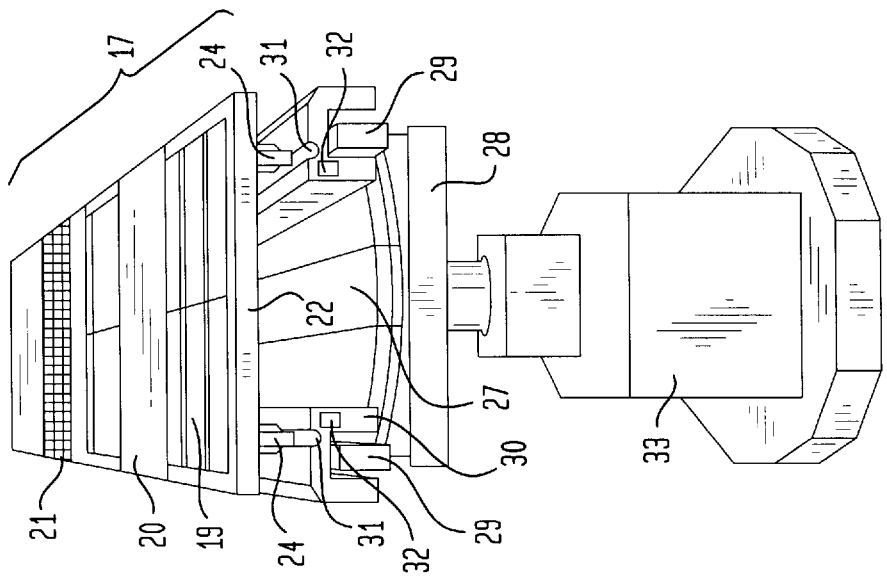
FIGS. 11A and B illustrate the complete assembly of the CT table and the accelerator table with the modified flat table top insert as the primary transport and which is moved forward to show part of the secondary transport of the CT table and the accelerator table.

FIGS.11 A and 11B show the end views of the CT and the accelerator tables with the modified flat table top insert above. Both tables are modified for the travel of the modified flat table top insert's rollers 24 over the grooves 25 of the CT cradle 13 and grooves 31 of the accelerator cradle 27. The modified table top insert's mylar 19, wood top 20, tennis racket 21, and its non-metallic frame 22 are identical to those of a commercial accelerator's table top on which the patients are placed for treatment. FIG. 11A is the CT table with the modified table top insert 17 on the grooves 25 of the CT table's cradle 13. At the rearward end of the CT cradle, two female notches 26 for connection with the accelerator table's cradle are also shown. The CT table's intermediate support 15, cradle 13, and the modified flat table top support rest on the elevator and base assembly 23 of the CT table.

Figure 11B:
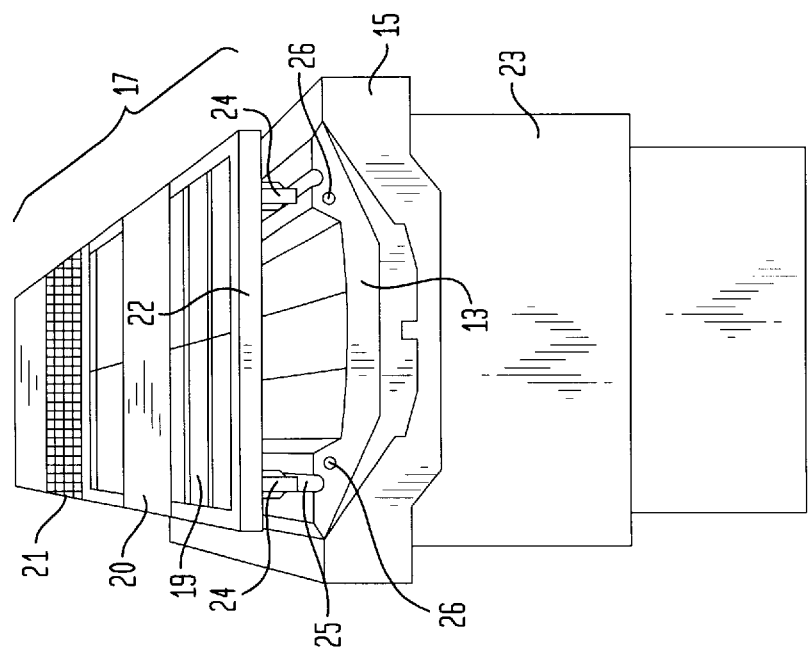

FIG. 11B shows the modified accelerator table with the modified flat table top insert 17 on top of the accelerator table's cradle 27. The regions of this modified table top insert 17, the mylar 19, wood 20, tennis racket 21, frame 22, the rollers underneath it 24 are all identical to the flat table top insert 17 on top of the CT table's cradle 13. The grooves 31 on accelerator table's cradle 27 are symmetrical to the grooves 25 on the CT table's cradle 13. The accelerator table's cradle's side rails 29 are fitted within the frame 30 with its grooves 31 on which the rollers 24 of the modified flat table top insert 17 can be rolled to the CT cradle or visa versa. The accelerator table's intermediate assembly 28, the cradle 27, and the modified flat table top insert 17 rest on the accelerator table's elevator and base assembly 33.

Figure 12:
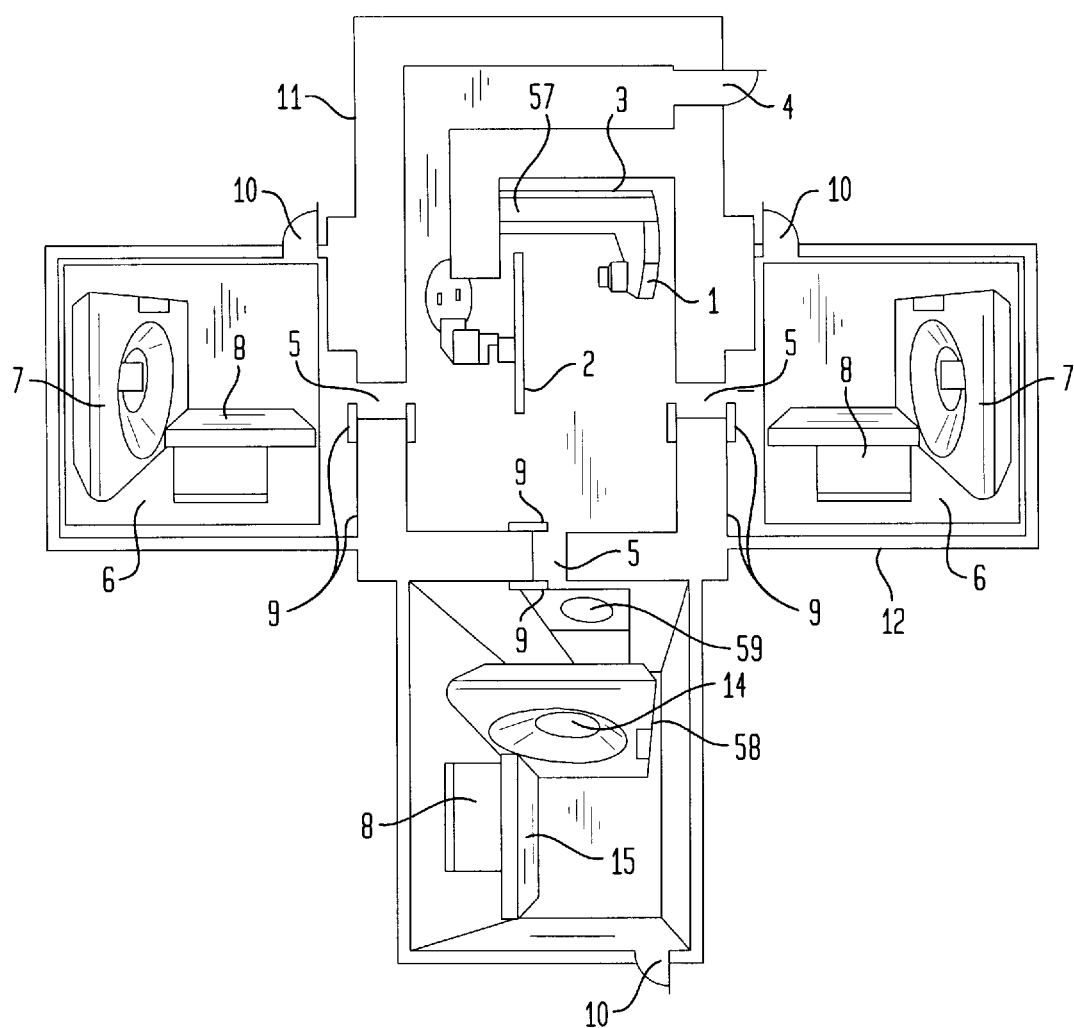
FIG. 12 is an illustration of an other arrangement of the CT and the accelerator to enable the treatment of a patient without rotating the table in one instance and with table rotation in another instance.
Figure 14:
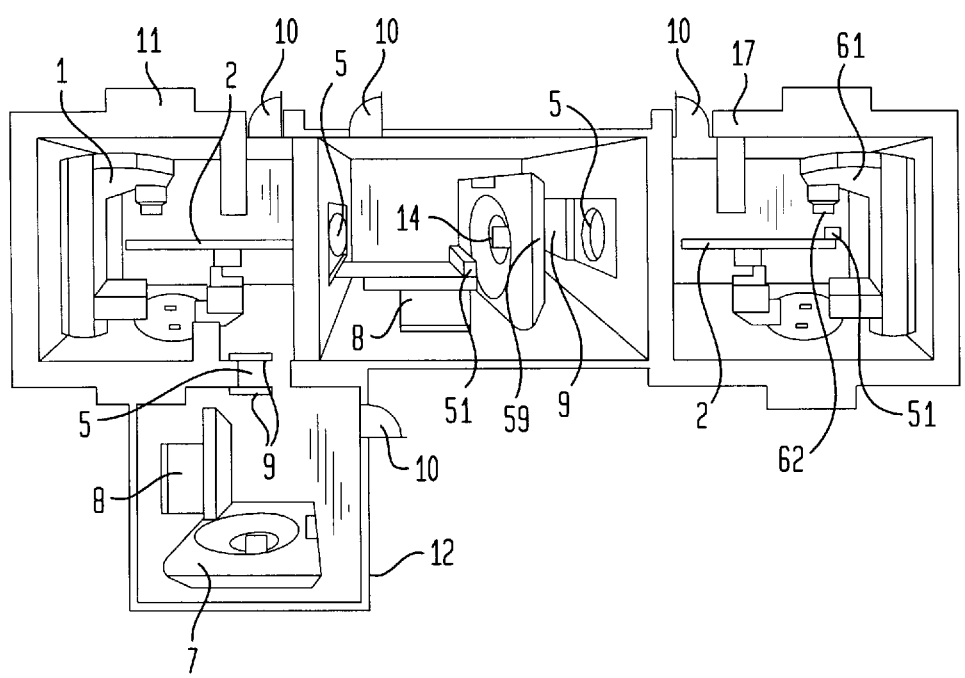
FIG. 14 is a modified embodiment of the invention wherein two accelerators, one for the routine radiation therapy and the other for special purpose radiation therapy is illustrated. After the setup of a patient on the CT table, the patient is moved through the wall openings to the respective accelerator table for desired treatment.

FIG. 12 is an illustration of another arrangement of the CT and the accelerator to enable the treatment of a patient without rotating the table in one instance and with table rotation in another instance. In first instance, the CT facing directly opposite to the accelerator's gantry 57 is placed in the CT room with the back side of the CT gantry 58 facing the wall opening 5. It is aligned with the wall opening for the forward transport of a patient on the modified flat table top insert through the CT's central opening and the wall opening to the accelerator table. As described above, an extension table 41 can be placed in between the CT's central opening's back side 59 and the wall opening 5. In the accelerator room, a similar extension table can be placed in between the wall opening and the accelerator table. With this arrangement a patient is first setup on the CT table and after the treatment port verification with the CT, the patient is then advanced forward through the CT's central opening's back side 59 and through the wall opening 5 to the accelerator room and to the accelerator table and placed directly under the accelerator's treatment head without a 180 degree rotation. If the CT is placed with its gantry's front facing the accelerator directly as shown in FIG. 1 and 14, and the patient's head is placed on the CT table with the head closer to the gantry and the foot at the rearward end of the CT cradle, the accelerator table needs to be rotated to 180 degree after the patient is transferred to the accelerator room to bring the patient's head region under the accelerator's treatment head. If a patient is placed on a commercially available CT table with the foot at the gantry end and the head at the table's rearward end, the CT of the head and the upper portions of the body can also be done. For this, a three foot extension to the forward end of the CT cradle may be needed. By doing so, portions of the head may not be in the CT plane. This is a major disadvantage, particularly for head and neck region's treatment. The straight transport of the patient either by reversing the position of the patient with the foot facing the gantry or by reversing the CT with the back of the CT gantry's central opening 59 facing the accelerator and moving the patient through the CT's back central opening to bring the patient's treatment region under the accelerator's treatment head eliminates the need for the accelerator table's rotation. This elimination of the table rotation further enhances the quality of conformal radiation therapy and the stereotactic radiosurgery. However as noted above, the reversing the position of the patient with the head away from the CT's gantry may not be suitable for this kind of treatment to the head and neck region. The CT positioned at 90 and 270 degree to the accelerator as in the second instance, will function as a combined unit with the accelerator by rotating the accelerator table to 90 degree to bring the patient under the accelerator's treatment head.

Figure 13A:
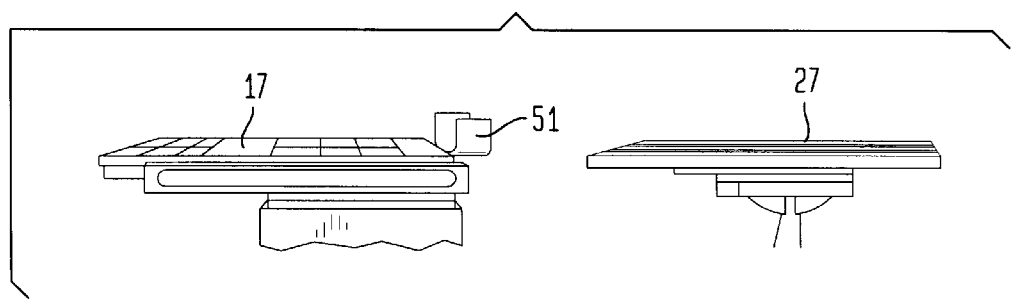
FIGS. 13A–C show a straight patient's transport from the CT to the accelerator with patient's upper body and the head brought under the accelerator's treatment head without table rotation and with table rotation for the CTs that are placed at 90 and 270 degree angles from the CT facing straight to the accelerator as in FIG. 12.
Figure 13B:
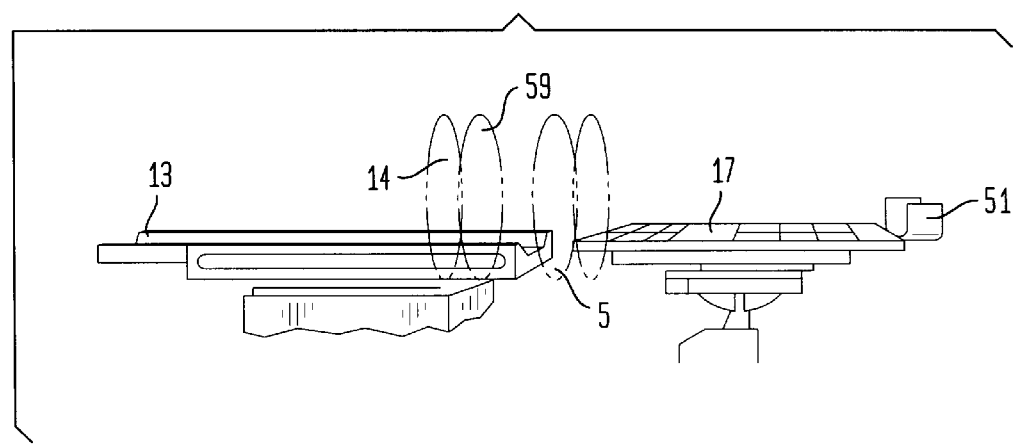
Figure 13C:
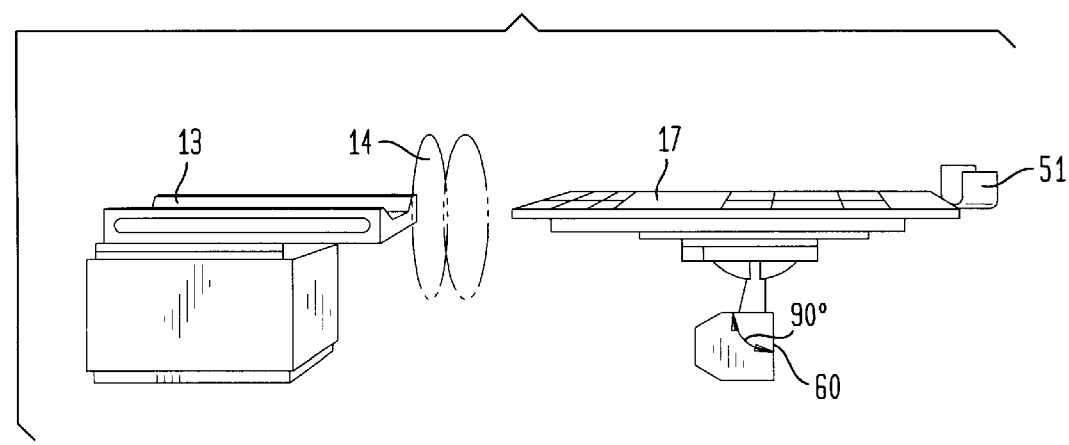

FIGS. 13A–C further illustrate the direct transport of the modified flat table top insert 17 from the CT cradle 13 towards the accelerator table's cradle 27, through the CT gantry's central opening's front 14, and its back 59, and wall opening 5. The table top insert is rolled over to the accelerator table's cradle 27, see FIG. 13A In this instance, no 180 degree rotation of the accelerator table is necessary to bring the patient's treatment site under the accelerator's treatment head as in FIGS. 10A–C. If the CT facing directly opposite to the accelerator is placed with the front of the gantry facing the accelerator (FIG. 1, 14) and the patient is placed in the usual manner with the head in the head holder which is closer to the gantry and the foot at the rearward end of the CT table, then a 180 degree rotation of the accelerator table is required to bring the patient's head with the head holder 48 under the accelerator's treatment head. With the presently available commercial CTs, a reverse patient's setup on CT table with the patient's head away from the gantry's central opening is impractical since the difficulties associated with the geometrical positioning of the head for its satisfactory scanning. In this position however the scanning of the upper portions of the body can be done by attaching an extension of about three foot to the CT cradle's forward end and placing the patient in a manner to make use of this table extension. By doing so, a patient after setup and scan can be transferred to the accelerator table and brought under the accelerator's treatment head without the accelerator table's rotation, see FIG. 13B In contrast to this direct transport of the modified flat table top insert 17 towards the accelerator's treatment head, FIG. 13C shows a 90 degree rotation 60 of the accelerator table to bring the patient under the accelerator's treatment head when the CTs are placed at 90 or 270 degree (FIGS. 1, 12, 14) to the accelerator. For critical procedures such as the conformal radiation therapy and the stereotactic radiosurgery, the ability to bring the patient's treatment site without this rotation is an added advantage for precise positioning of the patients and for the delivery of the planned treatment precisely.

The configuration as shown in FIG. 14 with two accelerators 1 and 61, two CTs 7 and the CT tables 8, with respective openings 5 in the walls for transport of the modified flat table top insert 17 with the patient's head holder 51, the accelerator tables 2, and the sliding shield doors 9, facilitate the routine daily radiation therapy with one accelerator 1 and the specialized treatment such as the stereotactic radiosurgery with other accelerator 61. In this case, the second accelerator 61 can be used as a dedicated one for special procedures such as the stereotactic radiosurgery, intraoperative radiation therapy and conformal 3D radiation therapy. After the setup and verification of a patient on the CT table, the patient can be transferred to the accelerator table through the back side of the CT gantry's central opening 59, and through the wall opening 5 directly described above, without any need for the accelerator table's rotation.

Permanently or semi-permanently, this special purpose accelerator 61 can be equipped with the necessary field shaping collimator 62 for special procedures such as the stereotactic radiosurgery or intraoperative radiosurgery at those Radiation Oncology centers where these procedures are frequently done. Of course both these accelerators 1 and 62 can be fitted with the special field shaping collimators and can be used for the special procedures. The advantage of equipping one accelerator in the configuration as with the accelerator 61 with the CT in this FIG. 14 is that it can take the full advantage of the CT combined accelerator to improve the quality and the cost efficiency of such treatments. It improves the patient setup and field verification, eliminates the waiting time for access to an accelerator and the dead time for CT data transfer from the Radiology department to the Radiation Oncology department for treatment planning. At a Radiation Oncology Department where many stereotactic radiosurgeries are done, the weekly number of such procedures is limited to about four patients. It is because of the waiting for access to an accelerator, delay in CT data transfer from the Radiology department to the Radiation Oncology department for treatment, planning and the subsequent efforts to set up the patient on the accelerator table identically as the CT images was obtained at the Radiology department's CT. Excluding the waiting time for the access to the accelerator, the present turn-around time for the stereotactic radiosurgery is about four hours. The technical improvements of this invention not only reduces the turn-around time from four patients a week to many more, but also improves the quality of the treatment significantly. The improvement of the quality of this treatment is much more important than the cost savings. This invention significantly improves both the quality and the cost efficiency of these specialized radiation therapy and therefore makes them available to a large number of patients everywhere. The special field shaping collimator can also be fitted on to the accelerator setup as in FIG. 12 but at a sacrifice of accelerator time for the frequent change of the field shaping collimator and the need to wait for access to the accelerator until the daily regular patient's treatment have been completed.

The patient transport to the accelerator table and bringing the patient under the accelerator's treatment head from the CT facing directly to the accelerator 1, and the CT placed at 90 degree to the accelerator 1, is performed by a 180 degree rotation in the former instance and with a 90 degree rotation in the latter case. It is further described under FIGS. 10A–C and 12.

Figure 15:
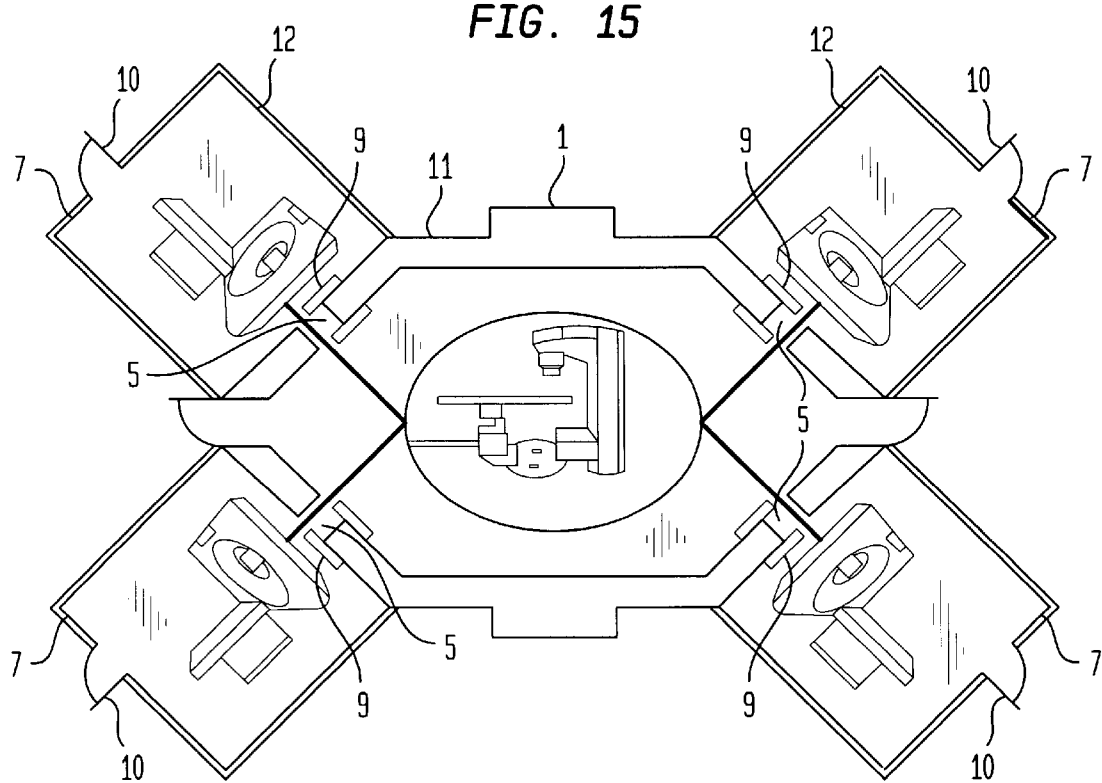
FIG. 15 is the top view of an other configuration of a single accelerator room connected to five adjacent CT rooms with their respective openings and shutters in the shared CT-accelerator wall

In FIG. 15, a different configuration of a single accelerator room with four CT 7, connected to it is shown. In this configuration, the accelerator 1 is centrally located, and the four CTs 7 surrounds it. As in FIG. 1, the wall openings 5 are opened and closed with sliding shield doors 9. The general operational features for the patient transport from the accelerator room to the CT rooms through the wall openings and bringing the patient under the accelerator's treatment head are generally as described in the transportation of the table top insert with the patient on an extension table. The main purpose of this illustration is to demonstrate that several CTs can be added to this CT combined with the accelerator for the cost efficient and improved quality radiation therapy of cancer and for the routine diagnostic imaging.

Figure 16:
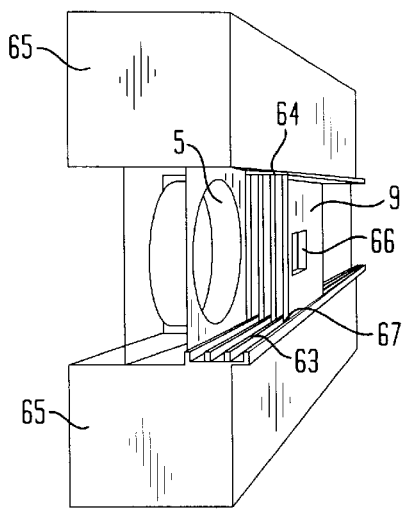
FIG. 16 illustrates the motor driven and the manual opening and closing of the sliding shield door and screws and support for attachment of additional thickness lead shields than the calculated thickness if after testing it is found to be necessary.

FIG. 16 illustrates the motor driven and the manual opening and closing of the sliding shield doors made of radiation protective metals and screws and its support mechanism. Provision is given for attachment of multiple slabs of heavy metal sheets 9c to make the weight of this mobile door to be distributed among the multiple individual metal sheets at the accelerator side's wall opening. At the side of the imaging room a single slab metallic sliding shield door 9d (FIG. 26) is attached as this is sufficient for the radiation protection from the diagnostic x-ray machine's kVp range of photon's energy and from the scattered radiation from the sliding shield door at the side of the accelerator room. The required thickness of the metallic sliding shield door is calculated based upon the common formulas integrating the workload (W), use factor (U), occupancy factor (T) and the distance (d). The wall opening for the transport of the patient from the CT room to the accelerator room is placed in the secondary barrier wall (Khan, F. M., Radiation protection; in The Physics of Radiation Therapy, $2^{nd}$ ed., 474–503, 1994; Shleien, B., Exposure and shielding from external radiation; in The radiation Physics and Radiological Health Handbook, 163–218, 1992).

The cross sectional view in FIG. 16 illustrates the sliding shield door as mounted on to the concrete wall. The metal channels 63 in the lower section of the concrete wall 65 and similar metal channels 64 in the upper section of the concrete wall 65 serve as the guide for the sliding door 9. It is fitted with a mechanical handle 66 to move to the opened and closed positions of the wall opening 5. The lower section of the sliding shield door is fitted with metal fasteners 67 as is further illustrated in FIG. 18. This door is compartmentalized as a series of slabs of doors which can be adjusted according to the required amount of shielding material needed for a particular sliding shield door. Also more of the weight of the shielding material is shared by these slabs than if the mobile door were made of a single compartment. The sliding shield door is driven to the open and closed positions by a motor driven mechanism when the weight of the sliding shield doors exceeds the limit that can be easily pulled and pushed by hand. Alternately to the sliding shield door, a conventional medical accelerator's beam shield can be adapted as sliding from one end of the wall opening to the other for the opening and closing of the wall opening with adequate shielding similar to the sliding shield door.

Figure 17:
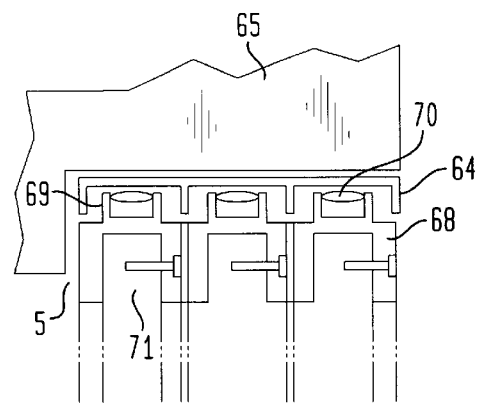
FIG. 17 shows the cross section of the top of the sliding shield door with metal fasteners, guide and rollers.

In FIG. 17 the cross section of the top of the sliding shield door is shown the door is comprised of the metal fasteners 68 with its guide 69 for its rollers 70 to slide through the metal channel 64. The shielding material 71 is threaded into the metal fastener 68. The top section of the sliding shield door is shown as attached to the upper portion of the concrete wall 65.

Figure 18:
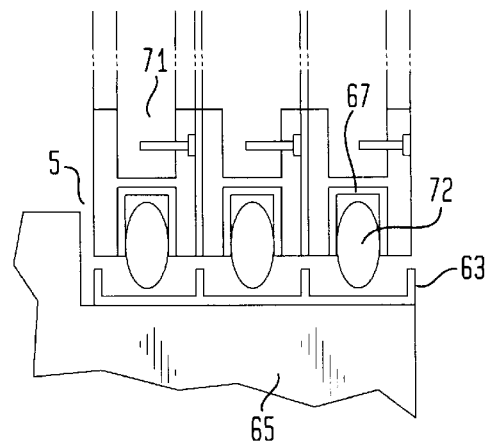
FIG. 18 demonstrates the cross section of the bottom section of the sliding shield door with its metal fasteners, wheels and metal channel.

FIG. 18 illustrates the cross section of the bottom portion of the sliding shield door. Its metal fasteners 67 are fitted with vertically installed wheels 72 for the sliding shield door's travel through the metal channel 63. The shielding material is screwed into the lower metal fasteners 67. This lower section of the sliding shield door is fitted on to the lower portion of the concrete wall 65.

Figure 19:
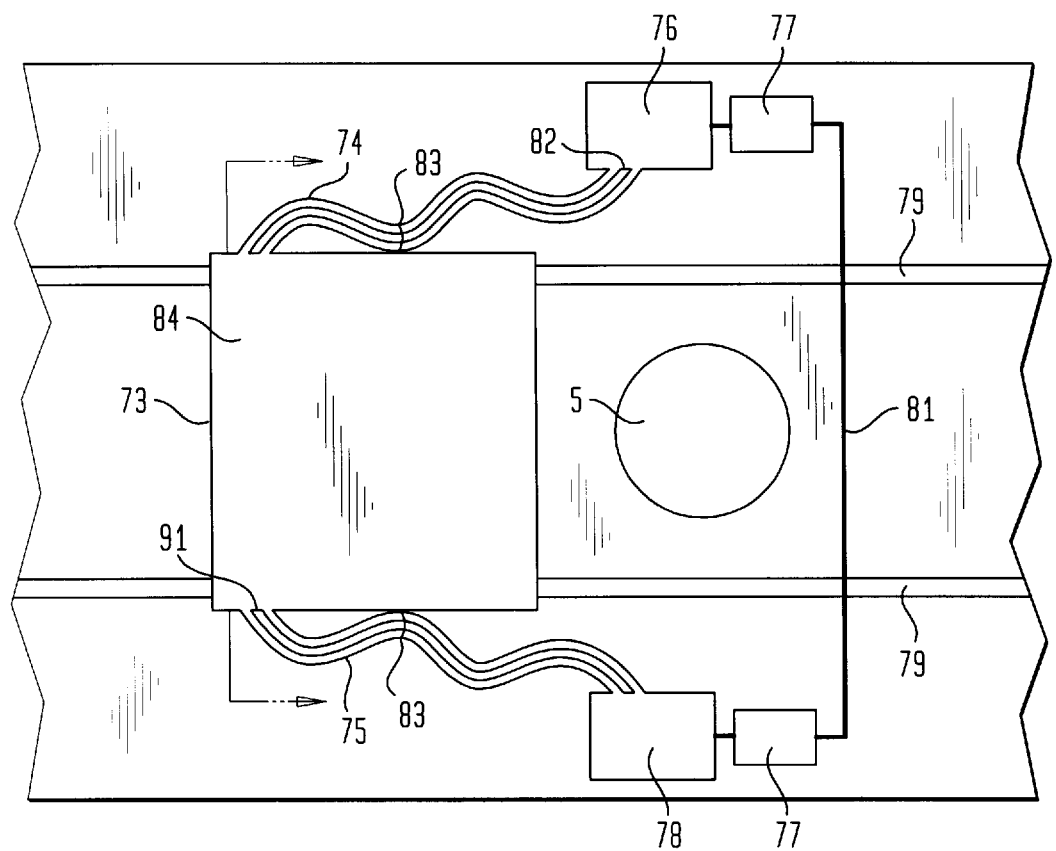
FIG. 19 shows the sliding shield door made of liquid shielding material with its hollow core door, reservoirs for the liquid shielding material, the pumps, the pipe line and the door's sliding mechanism.

In FIG. 19 an alternate method of constructing the sliding shield door is shown. In this case the shielding material is in liquid form which runs to the hollow core of the sliding shield door 73 which is installed with a set of inlet 74 and outlet 75 hoses. The core of this sliding door is divided into multiple cells. The number of cells filled with the liquid shielding material is based up on the required shielding for a given energy radiation and the position of the wall opening in relation to the accelerator. Whenever the wall opening 5 needs to be closed, the sliding hollow core door is pulled towards the wall opening and the hollow core door is kept in its locked position and filled with the liquid shielding material. The liquid shielding material is allowed to run from a reservoir 76 in the concrete wall at the top of the wall opening by opening the valve 82 (FIGS. 20 and 21) and through the hose 74 into the multi-cells of the sliding hollow core door. The valve 84 inside the hollow core door controls the fillings of the individual cells 86, 87, 88 (FIGS. 20,21). Simultaneously, the multi-cell's outlet valve 91 (FIG. 22) is closed to prevent the flow of the liquid shielding material through the outlet hose 75 at the bottom of the sliding hollow core door. The core of this hollow door is allowed to fill with the liquid shielding material 93 (FIG. 21). After filling the hollow core door with the liquid shielding material the flow valve 84 is brought into the closed position as in FIGS. 20 and 21. Simultaneously, the outlet valve 82 of the upper reserve tank is also brought to its closed position (FIGS. 20, 21 and 23). When the wall opening 5 is to be opened, the drain valve 91 (FIG. 22) at the bottom of the sliding hollow core door is released and the liquid shielding material is allowed to flow through the outlet hose 75 to a drain tank 78 located below the wall opening 5 in the concrete wall. The sliding hollow shield door is then moved away to the side of the concrete wall to open the wall opening 5. The sliding hollow core door rests upon its side on a metal channel 79. The door is fitted with rollers 92 and guide 80 (FIG. 21) to slide this door to open or close the wall opening 5. The clamps 83 are used to attach the loose mid portions of the hoses 74 and 75 to the top and the bottom of the sliding door so that they will not interfere with the movements of the sliding door. Two succession pumps in the concrete wall 77, one at the bottom and the other at the top of the wall opening 5, are connected to each other with a pipe line 81. The liquid shielding material is pumped from the draining tank 78 to the top reservoir 76 for the refilling of the sliding hollow core door for the next time when it is brought in position as a shield door in front of the wall opening 5. Adequate lead sheets are placed in front of the concrete where the fittings of the sliding shield door's accessory equipment have created defects in the required wall thickness.

Figure 20A:
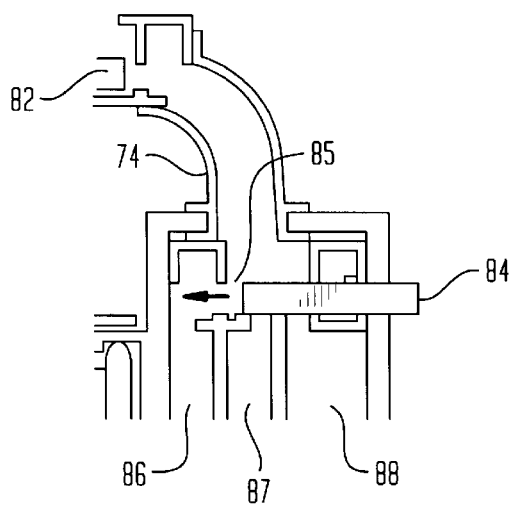
FIGS. 20A–C illustrate the top section of the opening and closing valves for control of the filling with of the hollow core of the sliding shield door with the liquid shielding material.
Figure 20B:
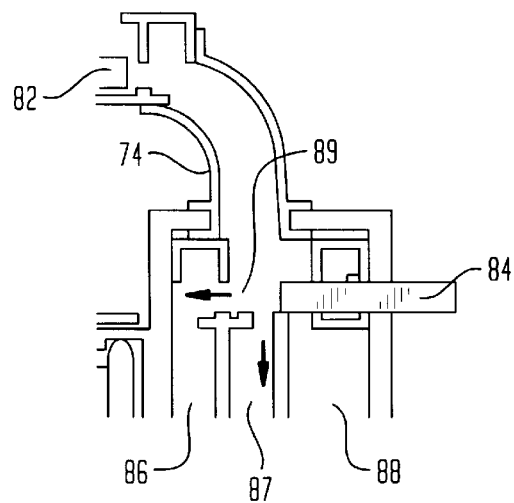
Figure 20C:
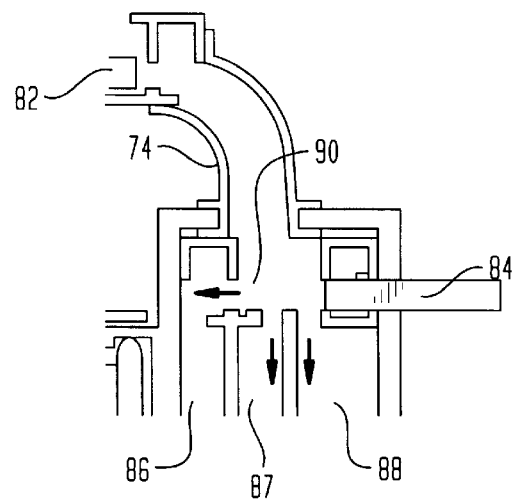
Figure 21:
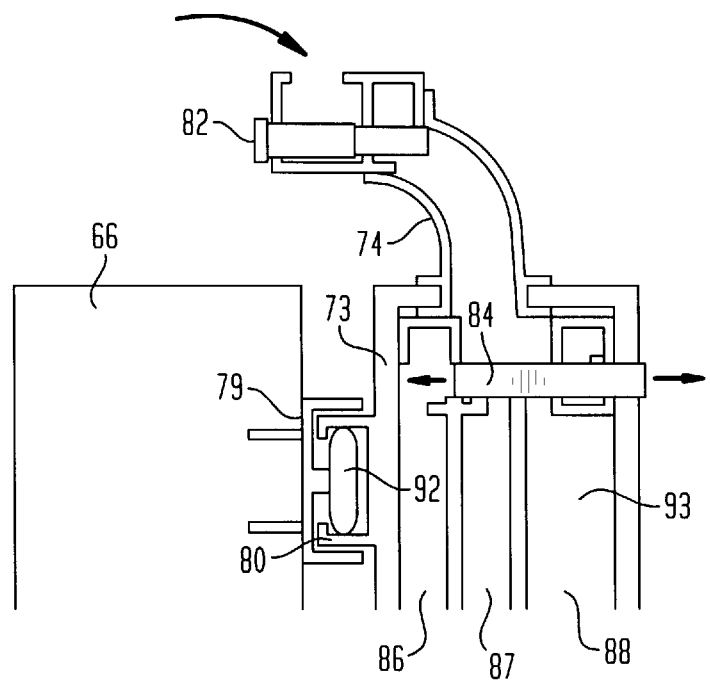
FIG. 21 shows the core of the sliding shield door after filling with the liquid shielding material and valve in its closed position.

FIG. 20 shows the cross section of the top of the sliding door with the inlet valve 82 which controls the individual cell's 86,87,88 filling with the liquid shielding material which flows through the hose 74 to the hollow core of the sliding door. The inlet valve 84 is moved from one cell to the other for each cell's filling. In FIG. 20A the filling of the first cell with the liquid shielding material is shown. The first partial movement of valve 84 to the right allows the flow of the liquid shielding material to the first cell 86, through the first valve opening 85. In FIG. 20B, the valve 84 is moved further to the right to open the inlets 89 of the both first and the second cells 86,87 to allow the flow of the liquid shielding material into both these cells. In FIG. 20C, the valve 84 is moved further to the right to open the inlets 90 of all three cells 86, 87, 89 to fill all of them with the liquid shielding material.

By consecutive movement of the valve 84 towards the left, the inlets of the third, second and the first cells 88, 87, 86 are closed. Thus the cells are filled as one by one to meet the required thickness shielding material in the sliding shield door. It gives the flexibility to use the same multi-cell sliding hollow core door at various sites with the site specific required thickness shielding material. An alternative to the multi-cell hollow core door is the multiple single cell hollow core door which are connected individually to the reserve tank 76 and to the drain tank 78 and is attached to individual metal channel 79, guide 80, and the rollers 92. This arrangement gives the flexibility to distribute the weight of the liquid shielding material to multiple individual sliding hollow core doors. It is illustrated in FIG. 23. Sensor switches attached to the lateral sides of the hollow core door automatically stops the movement of the sliding door if it encounters any obstruction in its path. Interlocks connected between the sliding hollow core door and the accelerator assures the radiation beam on only if the required cells are filled with the liquid shielding material and the wall opening 5 is completely closed. When multiple diagnostic devices are combined to an accelerator, there will be multiple wall openings 5 as described before. If any of the wall opening is in open position, incompletely closed, or the sliding hollow shield door is incompletely filled with the liquid shielding material, the interlocks to the accelerator will prevent the accelerator from activating to produce radiation. The commercial accelerators are integrated with interlocks to check the status of the door opening. This interlock is connected to the interlocks of the sliding shield doors and the wall openings.

In FIG. 21, the top section details with the inlet valve 84 in its closed position after filling the sliding hollow core door's cells 86,87,88 with the liquid shielding material 93 and the closed position of the inlet valve 82 at the level of the inlet hose 74 is shown. The metallic channel 79 is screwed on to the concrete wall 65. The guide 80 and the roller 92 for the sliding movements of the door on the metallic channel are also illustrated.

Figure 22:
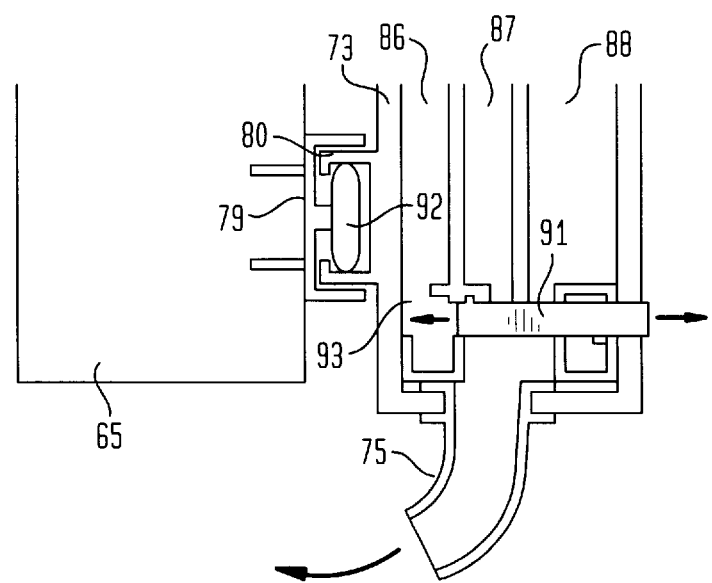
FIG. 22 demonstrates the sectional details of the bottom of the multi-cell sliding shield door. The outlet valve is shown as in its closed position.
Figure 23:
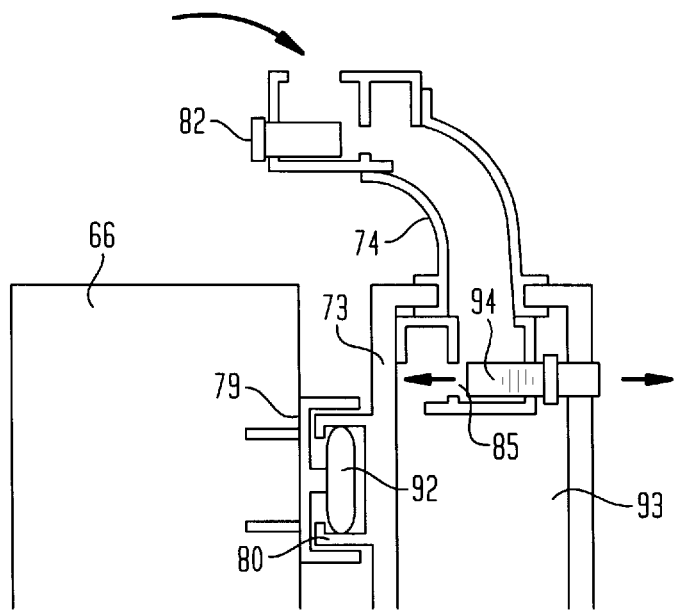
FIG. 23 and FIG. 24 illustrates the sectional views of the top and the bottom of a single cell sliding shield door.

FIG. 22 illustrates the sectional details of the bottom of the sliding shield door. The outlet valve 91 is brought to its closed position to prevent the flow of the liquid shielding material from the multi-cell compartments of the core 73 of the door to the outlet hose 75. The metallic channel 79 is screwed on to the concrete wall 65 at the bottom of the wall opening. The guide 80 and the rollers 92 aid in the sliding of the door on the metallic channel 79. The first second and the third cells 86, 87, 88 in the core of the door are filled with the liquid shielding material 93. When the sliding bottom outlet valve 91 is slid to the right, the valve is brought in open position and the shielding liquid material flows from the cells to the drainage tank 78 (FIG. 19) through the outlet hose 75. The valve is brought to the left to stop the drainage of the liquid from the cells by closing the outlets.

Figure 24:
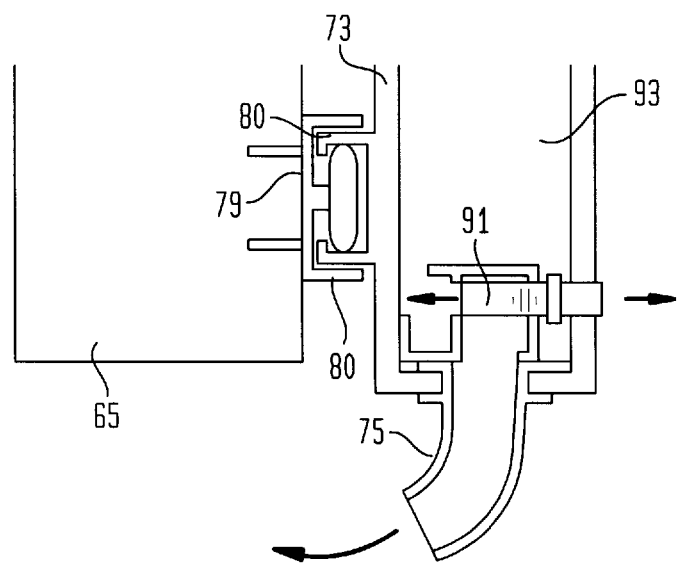

FIG. 23 demonstrates the sectional view of a single cell sliding shield door's top inlet and its sliding mechanism. Except for the single cell arrangement of the sliding shield door's core 73, the rest of the door, its inlet and outlet valve's operation and its sliding mechanism are similar to the top sectional view of the multi-cell sliding hollow shield door as illustrated in FIG. 21. In this case, only one cell needs to be filled by the inlet valve 94 with the liquid shielding material. Multiple single cell hollow core doors are connected individually to the reserve tank 76. The tank 76 is attached to individual metal channel 79 with guide 80 and the rollers 92. The single cell's drainage mechanism is similar to the multi-cell door's drainage system but with minor modifications. As shown in FIG. 24, each of the cells outlet hose 75 is connected to the drain tank 78.

FIG. 24 shows the sectional view of a single cell sliding shield door's bottom outlet and its sliding mechanism. Except for the single cell arrangement of the sliding shield door's core 73, the rest of the door, its outlet valve's operation and its sliding mechanism are similar to the bottom sectional view of the multi-cell sliding hollow shield door as illustrated in FIG. 22. In this case, only one cell needs to be emptied from the liquid shielding material by the outlet valve 91. Multiple single cell hollow core door are connected individually to the draining tank 78 by each door's drainage hose 75. As in FIG. 22, each single door's bottom section is attached to individual metal channel 79 for sliding of the door with guide 80 and rollers 92. The single cell arrangement gives the flexibility to distribute the weight of the liquid shielding material to multiple individual sliding hollow core doors. Each of these doors are brought in front of the wall opening 5 for its closure and moved away for its opening.

Figure 25A:
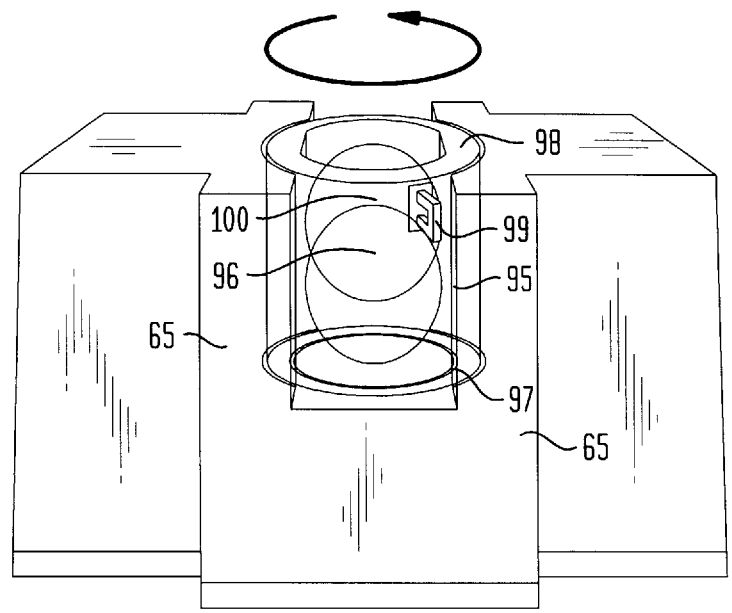
FIG. 25A and B show a rotating cylindrical shield with a central opening. It is fixed to the wall opening and brought to the open position or closed positions by a 90 degree rotation.
Figure 25B:
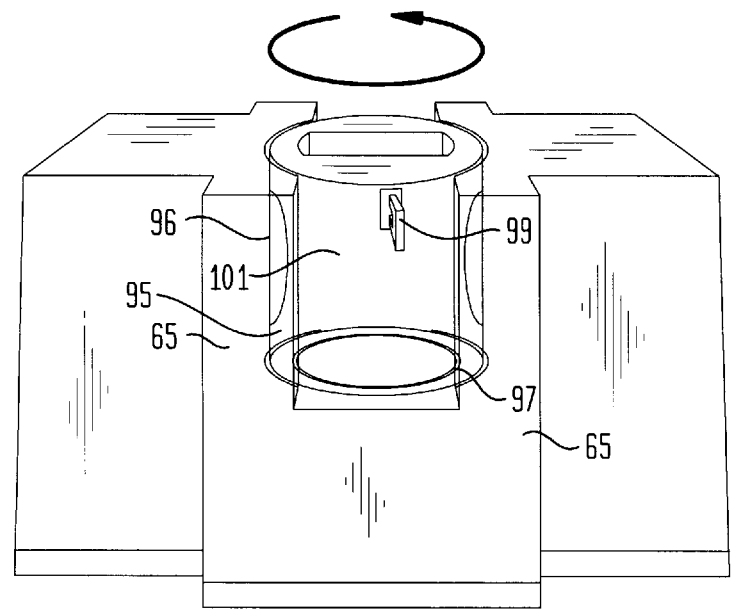

FIG. 25A and FIG. 25B demonstrate a different wall opening and closing mechanism than the previous ones. In this case, a rotating cylindrical solid shielding door 95 with a central opening 96 is inserted at the site of the wall opening 5. This cylindrical shield made of steel hollow core and filled with lead is made to rotate with the aid of motor driven chain mechanisms 97 which are attached to the top and bottom of this cylinder. This drive mechanism is inserted into the concrete wall which at the site of the wall opening 5 is modified at 98 for the accommodation of the cylindrical shield. The deficient thickness created in the concrete wall by attaching this drive mechanism is compensated with lead sheets. Also provision is made for the mechanical rotation of the cylinder in case of emergency with a retractable handle 99. In FIG. 25A, the wall opening 5 is brought to open position 100 by rotating the cylindrical shield to bring its opening to face the CT room on one side and the accelerator room at the other side. In FIG. 25B, the rotating cylindrical shield door 95 is shown in its closed position 101. The opening in the cylindrical shield door 96 is brought to horizontal to the concrete wall 65 so that this opening 96 now face the concrete wall 65 at both ends and the solid portions of this rotating cylindrical shield door faces the CT and the accelerator rooms and shields the both rooms from radiation. As described above, the safety of this cylindrical shield's operation during the opening and closing of the wall opening 5 is assured by safety interlocks. The accelerator's interlock for the door is connected to this cylindrical door. The accelerator will be activated only if the wall opening is closed completely and the cylindrical door is at a predetermined position to assure the required full thickness shielding of the wall opening is brought into position.

Figure 26B:
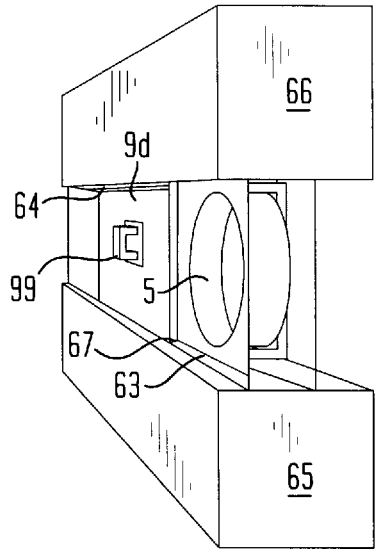
FIGS. 26A and B show the views of the sliding shield door from the accelerator room's side and the diagnostic room's side.
Figure 26A:
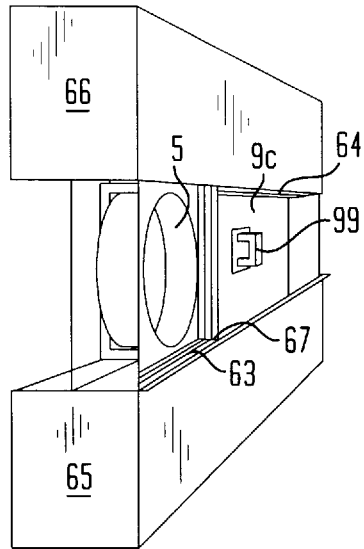

FIG. 26 is a view of the sliding shield door from the accelerator side of the wall opening and from the side of the diagnostic room. The wall opening 5 is shown in its opened position. In FIG. 26A, at the accelerator side, the configuration the sliding shield doors are as described above with reference to FIG. 16. Multiple slabs of shielding materials 9c are shown. In FIG. 26B, at the diagnostic imaging side of the wall opening, the opening and closing mechanism is as on the accelerator side except for the single slab sliding shield door 9d.

Figure 27B:
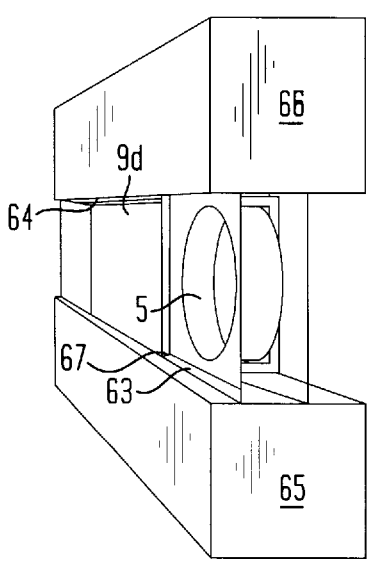
FIGS. 27A and B show the accelerator side's sliding shield door filled with the liquid shielding material and the diagnostic room shielded with a single sheet of sliding shield door.
Figure 27A:
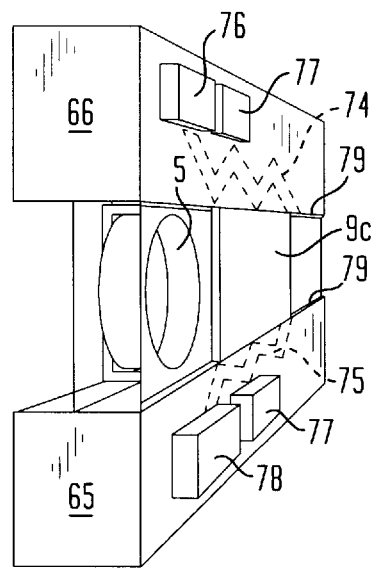

FIG. 27A is a view of the accelerator side's sliding hollow core door with the filling and draining of the liquid shielding material as was described with reference to FIG. 19. The opposite side of the wall opening 5 at the the diagnostic imagining device side, see FIG. 27B, is fitted with a single slab sliding shield door 9d as shown also in FIG. 26.

Figure 28:
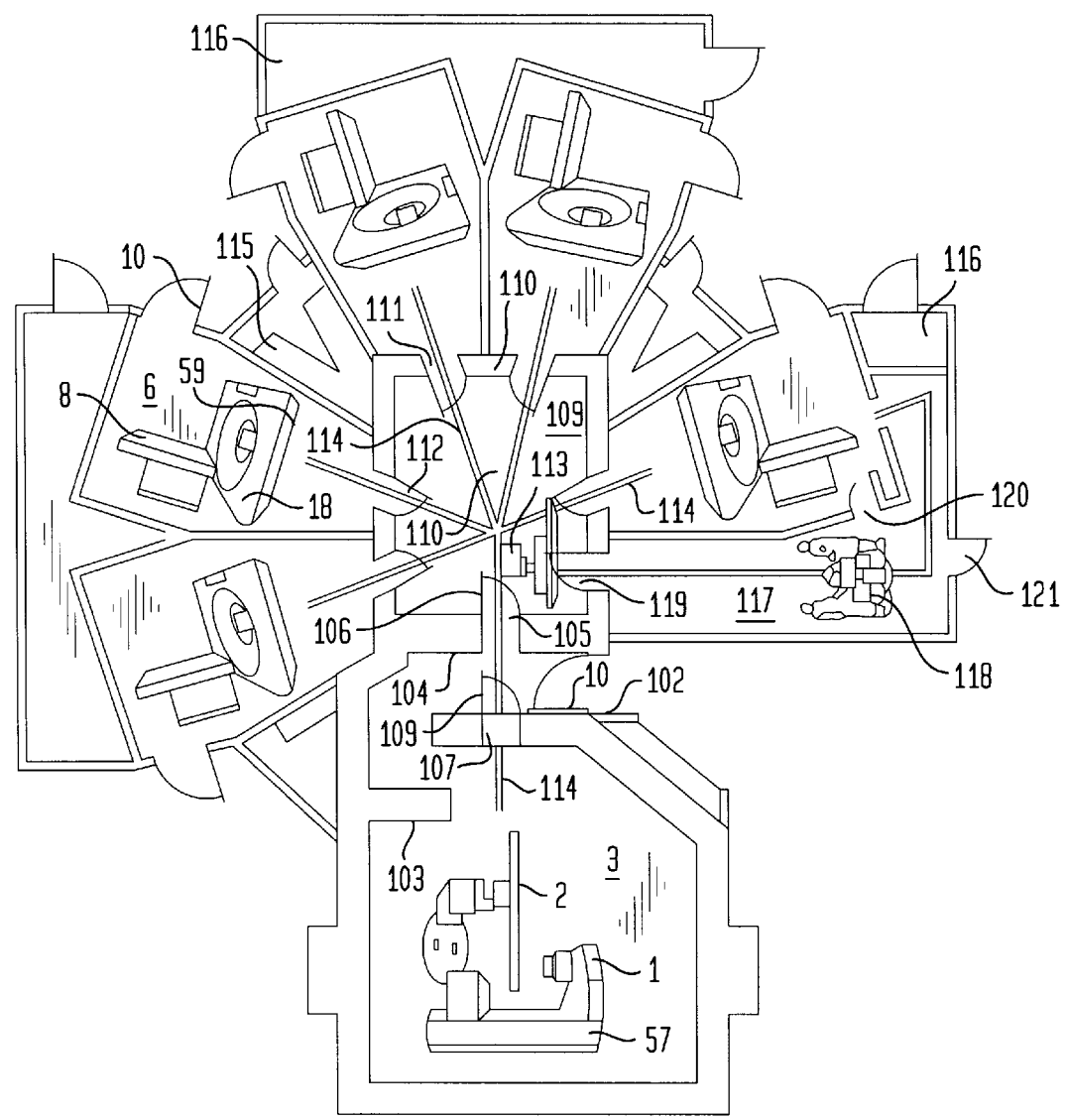
FIG. 28 illustrates an accelerator room with maze walls to reduce the energy of the radiation reaching to the opening of an ante-room space of the accelerator room. It drastically reduces the shielding requirement at the wall openings and allows to treat them as the door opening of a medical accelerator room. Multiple diagnostic devices and ancillary rooms for procedures such as surgery are attached to the common walls of these rooms with the wall of the accelerators ante-room space. The patient's transport from the diagnostic rooms table to the accelerator table is facilitated with an extension table that can be rolled on rails attached to the floor.

FIG. 28 illustrates a different configuration of the accelerator room with mazes to reduce the shielding at the wall opening. In this instance, the secondary barrier wall 102 in front of the accelerator table is interposed in between a shorter maze wall 103 and a longer maze wall 104. The longer maze wall 104 with the opening 105 for the door 106 and the shorter maze wall 103 circumvents the maze wall 102. The maze wall 102 has an opening 107 with a door 108. This opening 108 is at 0 degrees to the accelerator table. The double doors 108, 105 facing the opening 107, and the distance from the accelerator to the ante-room's wall 110 assure only a much decreased energy scattered radiation reaching these openings in the shared walls of the diagnostic room and the accelerator's ante-room. The openings in the concrete wall for patient transport from the diagnostic table are placed away from the direct path of radiation from the accelerator. By this arrangement only multiply scattered radiation with much reduced energy will reach the wall openings 111. In general, the construction of an accelerator room is done with maze walls to reduce the shielding requirement for door. With maze walls, the shielding for the door of a medical accelerator room is reduced to about less than 6 mm of lead for most facilities. The same principle of multiply scattered radiation with much reduced energy reaching the wall openings 111 for the connection of the accelerator room with the diagnostic room is applied here. Because of this reduced shielding requirement, the doors 112 at these wall openings 111 are treated the same as in the design of door for a medical accelerator. Such construction will also allow to make reduced thickness sliding shield door as was previously described in FIG. 16 and 19, however, the patient transport through a door opening is far more convenient than through the smaller wall opening 5. From the diagnostic table 8, the patient is transferred to a modified extension table 113 with rollers and is rolled on the tracks 114 leading to the accelerator. The back side of the diagnostic device's gantry's opening 59 faces the ante-room's wall opening 111 and its door 112. This allows the routine imaging of a patient with a device like the CT and the subsequent patient transport to the accelerator room. For imaging of the head and neck region, a head holder 51 (FIGS. 9A–C, 10A–C) is attached to the present CT. Through the rearward exit 59 of the gantry of the diagnostic device (FIG. 12) the patient is transported to the extension table and then to the accelerator table. The top section of this extension table 113 can be rotated to 360 degree to allow the patient's transport from any of the wall opening conveniently. This allows the patient to be placed on accelerator table with the head closer to the accelerator's gantry, which is the common treatment position of a patient on the accelerator table. Through the guide rails 113 the extension table with the patient is brought to the accelerator room. The accelerator 1 with its table 2 as retracted towards its gantry 57 to make room for attachment of the extension table is shown in the accelerator room 3. The flat table top insert 17 (FIG. 3) with the patient is rolled over to the accelerator table by rolling its rollers 24 on the grooves 31 of the accelerator table(FIG. 9,10 and 13). Only one patient at a time is brought to the accelerator's ante-room space 109. When the accelerator is idle, a patient whose setup and verification is completed is brought to the accelerator through the ante-room space 109. The extension table is connected to the accelerator table as described in FIG.7 before the patient's transfer to the accelerator table. The diagnostic rooms 6 with the table 8 and the gantry 18 are oriented towards the accelerator room at an angle to facilitate the transport of the extension table on the tracks attached on the floor at relatively straight paths. The diagnostic device's control room 115 and the utility room 116 are also shown in this figure.

In addition, an additional room 117 for special procedures such as surgery 118 is attached to the anteroom of the accelerator room through the door 119. Its door 120 opens to a diagnostic room while door 121 is for entry and exit from outside. This unique arrangement would greatly enhance both the quality and cost efficiency of the surgery combined 3-D conformal radiation therapy. The needed special surgical procedures can be done within the close proximity of a diagnostic device such as a CT or an MRI. At present, often surgery is done at a room far away from the diagnostic CT or MRI with the attempted correlation with the images previously obtained and subsequent transport of the patient to an accelerator from this distant operating room for the intraoperative 3-D conformal radiation therapy. The advantages associated with the availability of a surgical suite in association with a CT or MRI unit and the accelerator for improved quality and cost efficiency is obvious. It also facilitates the delivery of the brachytherapy combined surgery and 3-D external radiation therapy with greater precision due to the same advantages as the precise and online target treatment volume definition at surgery in a surgical suite in close proximity of an accelerator combined with a diagnostic device.

Figure 29:
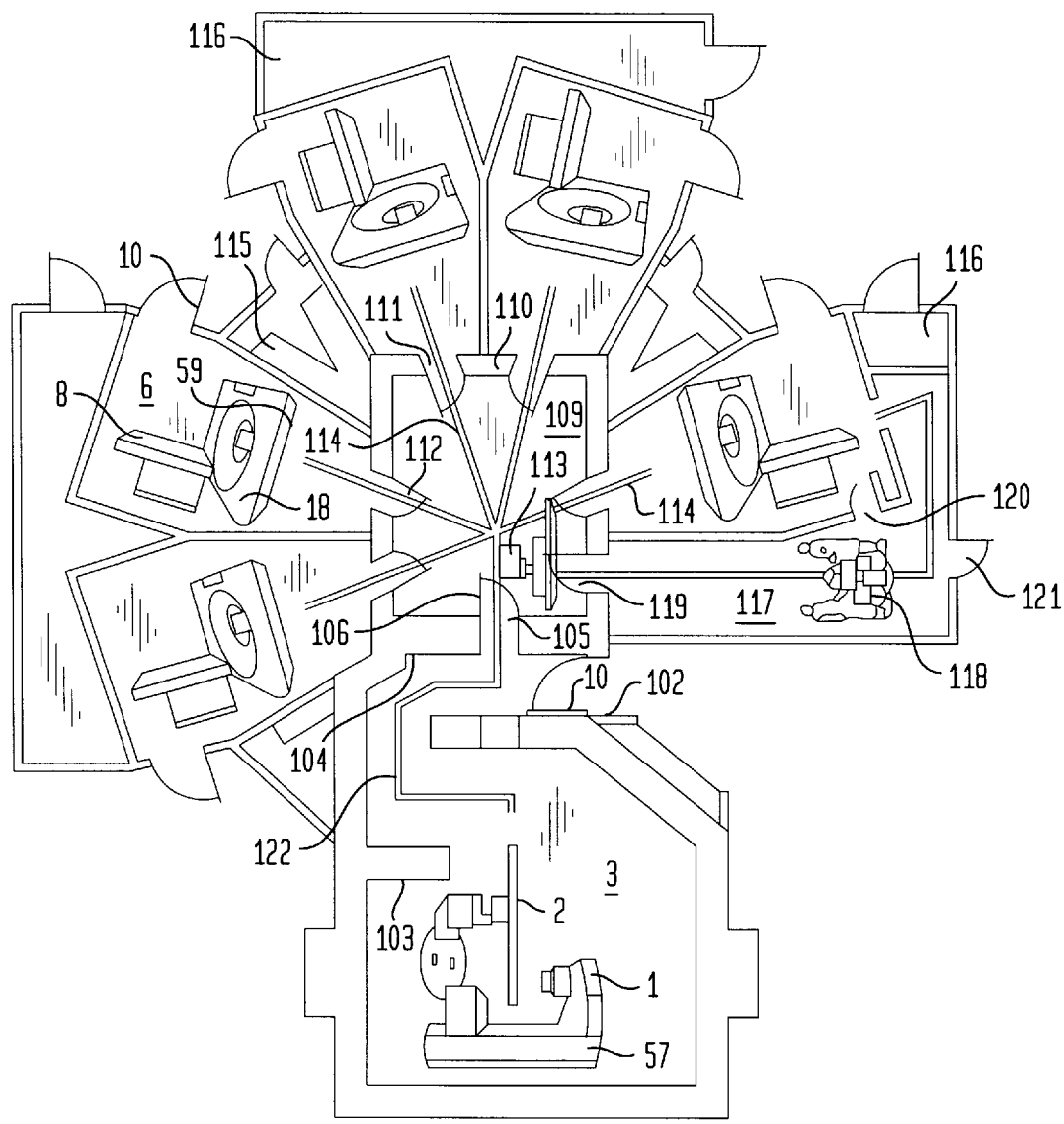
FIG. 29 is an other illustration of the same configuration of the structural features as in FIG. 28 but with modified maze wall 94 with no central opening and with the bending tracks on floor to circumvent the maze wall 94, to enter the accelerator room.

FIG. 29 is another illustration of a different configuration of the accelerator room with mazes to reduce the shielding at the wall openings 105, for entry to the accelerator room from the ante-room space 109 and the wall openings 111 at the shared wall of the diagnostic room and the ante-room. In this instance, the opening 107 in the secondary barrier 102 is eliminated. This further reduces the energy of the scattered radiation reaching the door 106 and the ante-room space's doors 112 and thus reduces the required shielding for these doors. It also allows one to construct the ante-room 109 with shielding equivalent to an x-ray room when the diagnostic device used in the adjacent diagnostic room is an x-ray generating unit such as a CT. The patient is transported from the diagnostic table 8 to the ante-room 109 through the door opening 112. From the diagnostic table 8, the patient is transferred to the modified extension table 113, as in FIG. 28, and is rolled on tracks 114 to the accelerator room. Track 114 begins at the diagnostic room and passes through the wall opening 111 to the ante-room 109 and enters the accelerator room with bending 122 to circumvent the barrier made by the maze wall 102. Except for these modifications, the structural and functional features as well as the identifying numerals shown in FIG. 29 are nearly identical to those in FIG. 28.

Figure 30:
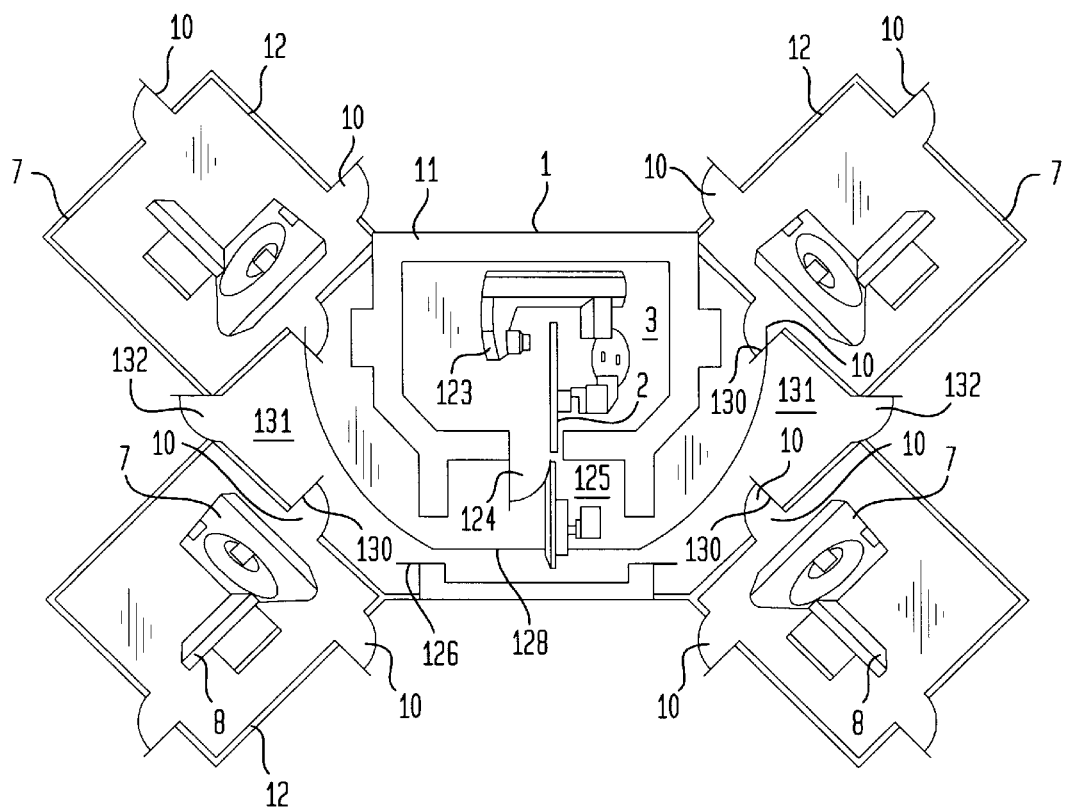
FIG. 30 is yet an other illustration of an accelerator surrounded my maze wall and the diagnostic devices attached to its hexagonal perimeter walls with openings for the patient's transport. This arrangement also reduces the energy of the radiation reaching the wall opening in the perimeter walls. It allows to treat these wall openings as for a medical accelerator's door design with much reduced shielding.

In FIG. 30, a modified version of the single accelerator 1 combined with multiple diagnostic devices 7 is shown. In this case, the configuration in FIG. 15 is modified with maze walls that surrounds the accelerator. The secondary barrier 123 in front of the accelerator table has an opening 124 for entrance and exit to the accelerator room 3 through this accelerator's anteroom 125. To reduce the weight of the door 126 at the opening 124 in front of the accelerator table, the door is made with less shielding material but the radiation that leaks through this door is absorbed by the ante-room's walls. The two sidewall doors 127 to the anteroom 125 allow entrance and exit to the anteroom. At these doors only, multiply scattered low energy radiation will reach and hence only much less shielding is required. A semi-circular curved track 128 on the floor surrounds the accelerator room. It connects with each of the diagnostic rooms 6 that surround the accelerator and passes through the anteroom 125. The diagnostic rooms 6 are arranged to form a hexagonal about the accelerator room. The track 128 runs through the floor in between the accelerator room and the diagnostic room. It is also connected to the accelerator room as it enters the accelerator room's floor through the secondary barrier's opening 124. A perpendicular track on the floor 129 runs from the anteroom to the accelerator room and ends in front of the accelerator table 2. It thus connects the semi-circular track 125 with the accelerator room. The extension table 113 is used to transport patients from the diagnostic tables 8 to the accelerator table 2. The diagnostic room's back exit door 130 opens to the secondary space 131 in between the diagnostic room and the accelerator room in the hexagonal arrangement of the diagnostic room around the accelerator. The initial patient setup and verification is done with the diagnostic device and subsequently, the diagnostic table 8 is extended to the secondary space 131 through the accelerator gantry's back exit 59 and the diagnostic room's back exit door 130. The extension table is rolled on the semi-circular rails 128 on the floor to bring it near to the diagnostic room's back exit door 130. The extension table's rotating table top section is rotated to the diagnostic table and both tables are connected together and the patient is transferred to the extension table. After disconnecting the tables, the extension table's top section is rotated to bring it back in parallel to the rails on the floor 128 and the extension table is rolled to the ante-room and then to the accelerator room on connecting rails 129. The patient is transferred to the accelerator table 2 by rolling the flat table top insert with the patient on the grooves 31 of the accelerator table's cradle (FIG. 11). In principle, the patient's transfer from the diagnostic table to the accelerator table is the same as described under FIGS. 7, 9, 10, 13, 28 and 29, but with the necessary adaptation for a given configuration of the room's layout. The entry and exit to the secondary room 131, in between the accelerator and its anteroom and the diagnostic room, is through the two doors 132 at both ends of the hexagonal layout of this configuration. The diagnostic rooms are equipped with entrance and exit doors 10. The accelerator room's greater thickness concrete wall 11 and the diagnostic rooms lesser thickness wall 12 are also shown in this illustrations.

Figure 31:
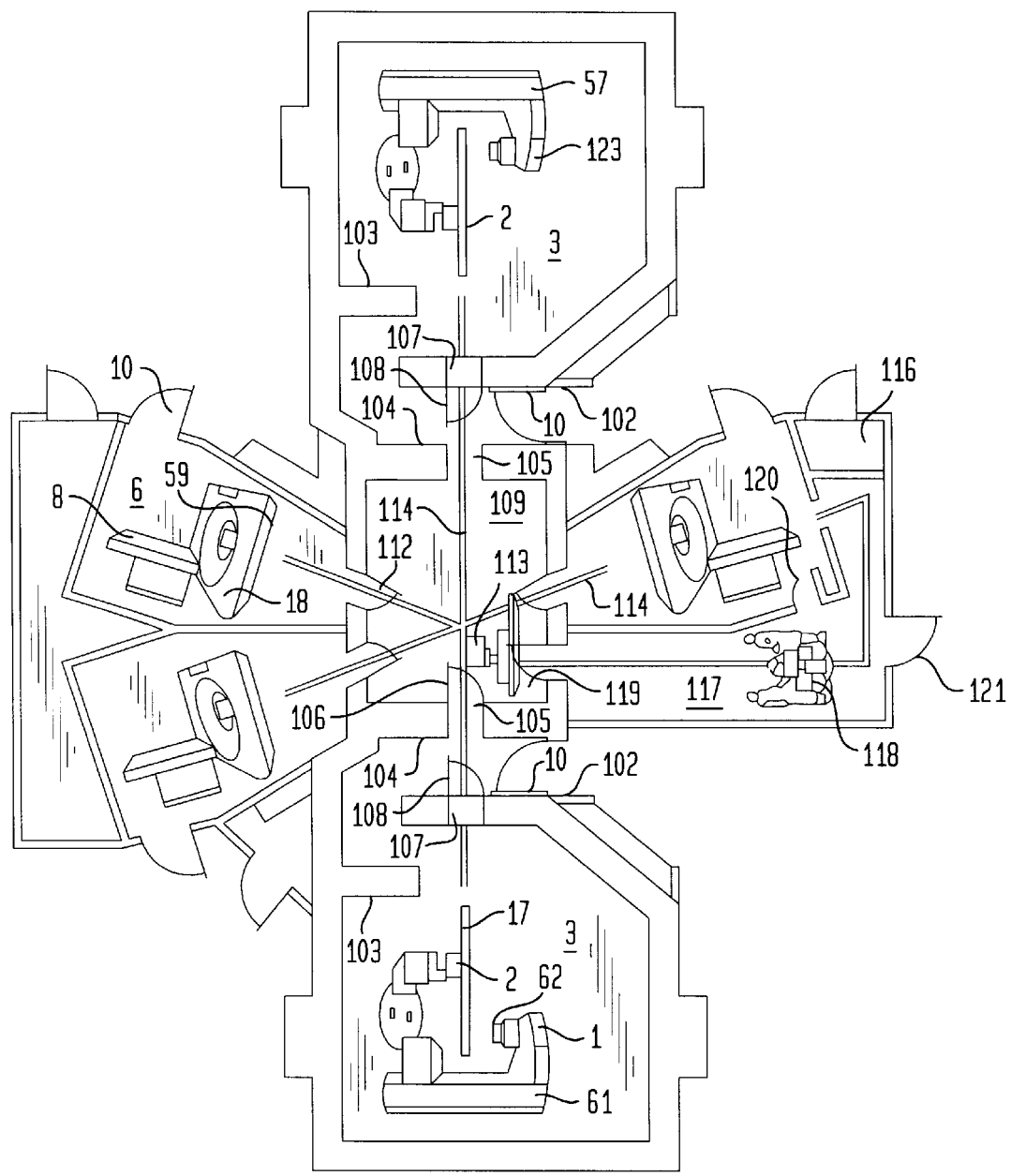
FIG. 31 illustrates two accelerators one at each ends of the ante-room and with multiple diagnostic devices. One megavoltage machine is configured closer to a surgical room and is equipped with special purpose collimator for special purpose megavoltage radiation therapy. The other megavoltage machine at the other end of the ante-room is without such modification and is for conventional radiation therapy.

FIG. 31 shows two accelerators with multiple diagnostic devices. The accelerator 1 is equipped with a special purpose collimator 62 for special procedures such as the radiosurgery and is configured at one end of the ante-room 109 and closer to the surgical room 117. The other megavoltage radiation therapy machine 123 is placed at the other end of the ante-room 109 and is a conventional accelerator for conventional megavoltage radiation therapy. The rest of the illustration identifying the parts of the diagnostic imaging device, the surgical room, the tracks, the extension table, the wall and door openings, and the maze wall arrangements are as described with respect to FIG. 28.

From the above descriptions, one skilled in the art would recognize the advantages of this invention including:

After the desired patient setup is done with the CT, the CT-table with the patient is moved towards an opening in the shared wall of the accelerator and the CT room. The accelerator table is also moved towards this common opening in the wall and the both tables are latched together. The patient is then brought to the accelerator table by moving the CT cradle towards the accelerator table. The patient is then transferred to the accelerator table without any changes in the patient's setup. Once the patient is moved to the accelerator table, the CT-cradle is retracted and the wall opening is closed with a protective shield for radiation protection. The CT-table is then aligned with the accelerator's treatment head and the radiation treatment is given to the desired anatomic region of the patient. After the treatment is completed, the patient leaves the accelerator room through its exit door and the next patient whose setup is completed in the next adjacent CT room is brought into the accelerator room and treated.

The disadvantage of the openings in the secondary barrier wall is that it will need doors with heavy shielding material. The required secondary barrier for the leakage radiation far exceeds the required secondary barrier for the scattered radiation in the megavoltage range. Unless a maze wall arrangement is made to prevent the direct incidence of radiation at the shield door, this door may weigh about 750 kg for a 6 MV accelerator beam. This heavy weight of the door is an inconvenience. In this case, the weight of the shielding door is distributed to multiple sliding doors. The sliding shield door is like the beam shield attached to an accelerator. Provisions for manual operation of these doors are also made. The arrangement without the maze walls has the advantage of easier patient transportation than the arrangement with the maze walls in between the secondary barrier.

With the maze walled accelerator room, the door openings are exposed only to the multiply scattered radiation of much reduced energy. Like the door shielding of an accelerator room, with maze walls interposed between the secondary barrier walls, the required shielding at the door openings for a usual accelerator room is reduced to about 6 mm thick lead. This allows larger wall opening to be made with reduced shielding for the door making the patient transport through the door easier. To take advantage of the reduced shielding requirement at the door openings when maze walled accelerator room construction is elected, this invention also includes construction of the accelerator room with maze walls. It also includes an anteroom to the accelerator room with required shielding. In this instance, the patient is first transferred from the diagnostic room to an ante-room to the accelerator through the shared doors between the diagnostic room and the ante-room and then to the accelerator room on extension table on rails. Whichever of these systems is elected is based upon the specific needs and the economical and the structural considerations of a specific treatment facility.

After checking for the satisfactory positioning of the patient on the accelerator table, the technical personal exits the room and the doors are closed. The shield door's interlock with the accelerator console assures the double check for the proper closure of the shield doors. If any of the doors are opened or improperly closed, the accelerator will not operate. Close circuit TVs monitors the patients and the inside of the accelerator room. A microphone and speakers at the control console maintain communication with the patient when the doors are closed. These precautions are the routine common practice in radiation therapy of patients and the commercial accelerators are equipped with such interlocks.

This configuration of multiple CT with one accelerator allows the rapid turnover of patients in the accelerator room. The time taken to deliver the usual about 200 cGy for daily treatment by the accelerator is typically less than a minute. The total time taken for the transport of the patient from the diagnostic table to the accelerator table, closure of the wall opening and the automatic accelerator's treatment setup as per each patient's initial plan and completion of radiation takes much less time than when the patient setup and treatment is done with the accelerator alone. For conventional radiation therapy, the former may take about less than 5 minutes while the latter may take at least about 20 to 25 minutes on the average. If the verification port films are also to be taken with the accelerator, the time taken by the accelerator to complete a patient's setup and treatment can almost double the routine daily treatment. During 3D conformal radiation therapy like the radiosurgery for intracranial lesion the average time taken is much longer. Therefore at present only about four patients are treated by stereotactic radiosurgery for intra-cranial lesions per week. Because of the reduced time taken for a patient's treatment at the accelerator, about for to five time more patients can be treated with a single accelerator, enhancing the cost-efficiency of this system. At present, a diagnostic device like a CT scan is much cheaper than the accelerator and hence addition of multiple diagnostic devices like the CT scans would not increase the overall cost of this system.

In this invention, the daily patient setup is verified by the CT with much superior anatomical delineation of the tumor site and its surrounding normal tissue before each day's treatment. The present existing methods of radiation therapy with accelerator do not have this capability. The changes in the body contour due to loss of weight swellings or other reasons, the changes in the tumor volume under treatment and its changing anatomical relation to its surrounding normal structures and the accurate estimation of the geometric outline of tissue inhomogeneities of the treatment regions are all estimated with the daily setup CT image. This CT image is used for the daily on-line CT integrated dosimetric calculations with a treatment planning computer. It is displayed on a TV monitor as superimposed on the daily setup CT image. A commercially available treatment planning computer is integrated with the CT combined accelerator system for the daily treatment verification. For the daily treatment setup and verification, only orientation one or two CT slices may be needed and hence patients are not kept long on the CT table. This greatly improves the overall quality of the daily dosimetric calculations and the quality of daily treatment. It also adds to the ease with which the daily treatment setup is done and the treatment port with superimposed dosimetry is verified. Such on-line quality control checkup before each day's treatment is presently not available and is not feasible.

The CT combined accelerator as in this invention, also improves the quality and the cost efficiency of conformal radiation therapy. It improves the patient setup and field verification, eliminates the waiting time for access to an accelerator and the dead time for CT data transfer from the Radiology department to the Radiation Oncology department for treatment planning. The technical improvements of this invention facilitates the stereotactic radiation therapy of many patients a day than the present four patients a week. It also improves the quality of this treatment significantly. The improvement of the quality of this treatment is much more important than the cost savings; but through the significant cost savings of this invention, very many patients can benefit from this advanced form of radiation therapy.

In brief, this invention's capabilities allow the improved quality and highly cost effective radiation therapy for cancer as the following. The patient is brought to the CT room and is placed on the CT table in the desired treatment position. When needed, the patient position is further secured with patient immobilization devices. Port verification limited CT are taken for comparison with the initial setup and the treatment plan. With the aid of a treatment planning computer, the initial setup treatment plan is superimposed on this CT for comparison. This enables the daily on-line verification of the setup and dose distribution of the intended treatment. After making the necessary adjustments in the setup if necessary, the motor driven CT table with the patient on it is advanced towards the opening in the wall or to the accelerator's ante-room. When the patient is transported through the wall opening, the accelerator table from the adjacent accelerator room is also brought to the opening in the wall. The tables are connected and fastened together. Through the track on the table tops, the patient is moved from one table top to the other and thus brought from the CT room to the accelerator room. After closing the wall opening with the sliding shield door, the CT room and the accelerator rooms are separated and functions independently of each other. The patient on the accelerator table is placed under the accelerator's treatment head and the treatment to the desired anatomical site as was setup and verified with the CT is given. In the alternative arrangement with an ante-room to the accelerator, after the patient setup and verification in the CT room is completed, the patient is transferred from the CT table to an intermediate accelerator table and which is then rolled on tracks attached on the floor of the ante-room and leads to the accelerator room. The patient is then transferred to the accelerator table. After completion of the treatment, patient leaves the accelerator room through its door. In the CT room, a new patient setup will begin. The time taken to complete the radiation with the accelerator is much shorter than the patient setup and verification with the CT. This difference in time taken for setup and verification by the CT and the actual treatment by the accelerator allows treatment of several patients with one accelerator within the time period of a single patient setup and verification by the CT. This allows another patient to be brought into the accelerator room whose setup and verification has completed with an other adjacent CT. This follows another patients radiation treatment whose setup and verification is completed in an other CT room. Whenever the accelerator room and the CT rooms function independently, all the connecting wall openings and doors are closed. In this manner, a single accelerator can treat very many patients with much higher accuracy than when the patient setup, verification and the treatment all are done with the accelerator. It also reduces the turn-around time for 3D conformal radiation therapy and stereotactic radiosurgery while improving the quality of this treatments further as described earlier. When the diagnostic device is not in use with the accelerator, it is used as a stand alone imaging device of a diagnostic Radiology Department. All these combined advantages of this invention provides a great deal of cost savings in the radiation therapy of cancer while the quality of this cancer treatment is many fold improved.

The disclosure of the invention described herein above represents the preferred embodiments of the invention; however, variation thereof, in the form, construction and arrangement of the accelerator and the CT thereof and modified application of the invention are possible without departing from the spirit and scope of the appended claims.

What is claimed is:

1. An improved patient handling system for use with a radiation therapy device and medical imaging device, comprising:

a first chamber having a radiation therapy device; a second chamber having a medical imaging device; and a first wall dividing said first chamber and said second chamber and having means defining a hole in said first wall for providing communication between said first chamber and said second chamber;

said first wall further having radiation shielding means including an open position allowing communication between said first and second chambers and a closed position for selectively covering said first wall hole defining means to seal said second chamber from radiation from the radiation therapy device in said first chamber;

a cradle located on the medical imaging device for receiving a table top insert and having means defining a groove on said cradle;

a cradle located on the radiation therapy device for receiving said table top insert and having means defining a groove on said cradle;

said table top insert having a patient securing means for securing a patient in a fixed position on said table top insert and having a lower surface for securing rollers to said lower surface and wherein said rollers are sized to fit within said groove of the medical imaging device and said groove of the radiation therapy device;

said means defining said hole in said first wall being sized and positioned such that said table can be rolled on said rollers from said medical imaging device cradle to said radiation therapy device cradle without changing the position of the patient.

2. An improved patient handling system according to claim 1 further wherein said radiation shielding means includes a sliding shield door having a hollow core for receiving a liquid shielding material;

said radiation shielding means further including an upper reserve tank in said wall for receiving said liquid shielding material, a lower reserve tank in said wall for receiving said liquid shielding material, at least one pump for pumping said liquid shielding material from said lower reserve tank to said upper reserve tank, a valve in said sliding shield door for selectively allowing said liquid shield material to flow from said upper reserve tank to said hollow core, and an outlet valve for selectively allowing said liquid shield material to flow from said hollow core to said lower reserve tank.

3. An improved patient handling system according to claim 2 further wherein said radiation shielding means includes lead, concrete, and liquid metals.

4. An improved patient handling system according to claim 2 wherein said radiation shielding means includes a plurality of doors each having rollers; and said first wall includes a concrete portion for slidingly receiving said rollers on said plurality of door rollers and driving means for driving said plurality of door rollers for sliding said plurality of radiation shielding doors.

5. An improved patient handling system according to claim 4 wherein said driving means includes a motor.

6. An improved patient handling system according to claim 4 wherein said plurality of radiation shielding doors have means defining a hollow core therein for receiving a liquid shielding material.

7. An improved patient handling system according to claim 6 wherein said liquid shielding material is a metal.

8. An improved patient handling system according to claim 6 further wherein said liquid metal is a Lipowitz metal.

9. An improved patient handling system according to claim 8 wherein said Lipowitz metal is substantially 70 degrees Celsius.

10. An improved patient handling system according to claim 1 further comprising:

a third chamber having a second medical imaging device and a second wall dividing said first chamber and said third chamber and having a second means defining a second hole in said second wall for providing communication between said first chamber and said third chamber;

a cradle located on the second medical imaging device for receiving a table top insert and having means defining a groove on the second medical imaging device cradle for receiving the table top insert rollers;

said second means defining said second hole in said second wall being sized and positioned such that said table can be rolled on said rollers from said second medical imaging device cradle to said radiation therapy device cradle without changing the position of the patient.

11. An improved patient handling system according to claim 10, wherein the medical imaging device includes a gantry having means defining an opening for receiving the patient and said table top insert on said medical imaging cradle in said opening; said gantry further includes an entrance and an exit; and wherein said first wall is intermediate said medical imaging device gantry exit and the radiation therapy device.

12. An improved patient handling system according to claim 10 further wherein the radiation therapy device is selected from a Computed Tomography device, Magnetic Resonance Imaging device or a simulator combined with a Computed Tomography device.

13. An improved patient handling system according to claim 10 further wherein the radiation therapy device is selected from either a medical linear accelerator, a cobalt-60 machine, or a medical microtron.

14. The improved patient handling system according to claim 1, further comprising:

an antechamber adjacent to said first chamber via a door opening;

a means for communicating between said antechamber and said first chamber, wherein said means for communicating reduces shielding requirements between said first chamber and said antechamber; and a plurality of second chambers adjacent to said antechamber such that said first chamber communicates with said plurality of second chambers via said antechamber and said means for communicating;

whereby a patient is transported on said table top insert from one said second chamber to said first chamber on top of an extension table via said antechamber with minimal change in position of the patient on said table top insert.

15. The improved patient handling system according to claim 14, wherein said means for communicating between said antechamber and said first chamber is a plurality of walls in said first chamber creating a maze configuration, thereby reducing scattered radiation reaching said maze configuration.

16. The improved patient handling system according to claim 15, wherein said plurality of walls comprises:

a short maze wall; and a long maze wall having a hole opening for a patient's transport, said hole opening aligned with said door opening.

17. The improved patient handling system according to claim 14, further comprising an operating room;

a means for connecting said operating room to one said second chamber; and a means for connecting said operating room to said antechamber.

18. The improved patient handling system according to claim 17, wherein said antechamber reduces scattered radiation from the radiation therapy device in said first chamber that reaches said operating room and said second chambers.

19. The improved patient handling system according to claim 17, wherein said means for communicating between said antechamber and said first chamber is a plurality of walls in said first chamber creating a maze configuration, thereby reducing scattered radiation from the radiation therapy device in said first chamber that reaches said antechamber, said second chambers and said operating room.

20. The improved patient handling system according to claim 14, further comprising a method of transferring a patient secured to a table top insert on said cradle of the medical imaging device from one said second chamber to said first chamber via said antechamber, wherein said method of transferring the patient comprises the steps of:

a. advancing said table top insert on said rollers of said table top insert within said grooves of the medical imaging device such that said table top insert extends over the medical imaging device's back exit and into said cradle of said extension table;

b. advancing completely said table top insert onto said extension table;

c. advancing said extension table from said second chamber to said antechamber through a door opening;

d. advancing said extension table from said antechamber to said first chamber through said door opening;

e. advancing said table top insert on said rollers of said table top insert within said grooves of said extension table such that said table top insert extends over an end of said extension table and into said cradle of the radiation therapy device; and f. advancing completely said table top insert onto the radiation therapy device such that a treatment site of the patient is under the radiation therapy device's treatment head.

21. The improved patient handling system according to claim 14, further comprising:

one or more rails on the floor connecting the radiation therapy device in said first chamber, said antechamber, and the medical imaging devices in said second chambers; and an extension table with a cradle having means defining a plurality of grooves on said extension table wherein said grooves of said extension table are sized to receive said rollers of said table top insert, thereby engaging and guiding said table top insert, and having a means for traveling along said rails;

wherein the patient is transferred between said first chamber, said antechamber, and said second chambers on said table top insert on said extension table by traveling along said rails.

22. The improved patient handling system according to claim 1, further comprising an extension table having means defining a plurality of grooves on said extension table wherein said grooves of said extension table are sized to receive said rollers of said table top insert, thereby engaging and guiding said table top insert.

23. The improved patient handling system according to claim 22, wherein said cradle of the radiation therapy device, said cradle of the medical imagery device, and said cradle of said extension table further comprise:

a means for latching together the radiation therapy device, the medical imaging device and said extension table;

a male notch; and a female notch;

whereby said male notch and said female notch are aligned when a radiation therapy device, medical imagery device or an extension table are latched together, thereby facilitating the transport of a patient on said table top insert.

24. The improved patient handling system according to claim 22, further comprising a method of transferring a patient secured to a table top insert on said cradle of the medical imaging device from said second chamber to said first chamber through a door opening in said first wall, wherein said method of transferring the patient comprises the steps of:

a. advancing said table top insert on said rollers of said table top insert within said grooves of the medical imaging device such that said table top insert extends over an end of the medical imaging device and onto said extension table;

b. advancing completely said table top insert onto said extension table;

c. advancing said extension table from said second chamber to said first chamber through the door opening;

d. advancing said table top insert on said rollers of said table top insert within said grooves of said extension table such that said table top insert extends over an end of said extension table and into said cradle of a table of the radiation therapy device; and e. advancing completely said table top insert onto the table of the radiation therapy device such that a treatment site of the patient is under the radiation therapy device's treatment head.

25. The improved patient handling system according to claim 14, further comprising:

a third chamber having a second radiation therapy device; and a means for communicating between said third chamber and said antechamber, wherein said means for communicating reduces shielding requirements between said third chamber and said antechamber.

26. The improved patient handling system according to claim 25, wherein said second radiation therapy device has a special collimator for three dimensional conformal radiation therapy or for radiosurgeries.

27. The improved patient handling system according to claim 1, further comprising:

a third chamber having a second radiation therapy device equipped with a special purpose collimator for three dimensional conformal radiation therapy or for radiosurgeries;

a second wall dividing said third chamber and said second chamber and having a means defining a hole in said second wall for providing communication between said third chamber and said second chamber; and said second wall further having radiation shielding means including an open position allowing communication between said third chamber and said second chamber and a closed position for selectively covering said hole in said second wall defining means to seal said second chamber from radiation from the second radiation therapy device in said third chamber;

wherein, in said second chamber, said medical imagery device's back exit faces said third chamber.

28. The improved patient handling system according to claim 1, wherein said first chamber is hexagonal in shape and said radiation therapy device is placed away from its primary beam's direction to take advantage of the distance traveled by scattered radiation; and a plurality of second chambers adjacent to said first chamber wherein each said second chamber has a first wall dividing said first chamber and said second chamber and a means defining a hole in said first wall and a radiation shielding means.

29. The improved patient handling system according to claim 14, wherein said first chamber, a heavily shielded room, and said plurality of second chambers are placed in a hexagonal arrangement, wherein said antechamber provides a barrier between said first chamber and said plurality of second chambers, such that a patient is transported from one said second chamber to said first chamber with a minimal change in position on said table top insert.

30. The improved patient handling system according to claim 1, further comprising:

a third chamber having a medical imaging device and a second wall dividing said first chamber and said third chamber and having means defining a hole in said second wall for providing communication between said first chamber and said third chamber, wherein the medical imaging device in said third chamber is placed at ninety degrees to the radiation therapy device in said first chamber such that the medical imaging device's front end faces the radiation therapy device, thereby allowing the placement of a treatment site of the patient under the radiation therapy device's treatment head with rotation of the patient; and a fourth chamber having a medical imaging device and a third wall dividing said first chamber and said fourth chamber and having means defining a hole in said third wall for providing communication between said first chamber and said fourth chamber, wherein the medical imaging device in said fourth chamber is placed at two hundred seventy degrees to the radiation therapy device in said first chamber such that the medical imaging device's front end faces the radiation therapy device, thereby allowing placement of a treatment site of the patient under the radiation therapy device's treatment head with rotation of the patient;

wherein the radiation therapy device is placed in said first chamber such that the radiation therapy device faces the back exit of the medical imaging device in said second chamber, thereby allowing placement of a treatment site of the patient under the radiation therapy device's treatment head without rotation of the patient.

31. The improved patient handling system according to claim 1, further comprising a method of transferring a patient secured to a table top insert in said cradle of the medical imaging device from said second chamber to said first chamber through said hole in said first wall, wherein said method of transferring the patient comprises the steps of:

a. advancing said table top insert on said rollers of said table top insert within said grooves of the medical imaging device such that said table top insert extends over an end of the medical imaging device and into said hole in said first wall;

b. advancing said table top insert on said rollers of said table top insert through said hole in said first wall and into said cradle of the radiation therapy device such that said table top insert extends through said hole and onto an end of the radiation therapy device;

c. advancing completely said table top insert onto a table of the radiation therapy device; and d. rotating the table of the radiation therapy device to bring a treatment site of the patient under the radiation therapy device's treatment head.

32. The improved patient handling system according to claim 1, further comprising a method of treating a patient secured to a table top insert without positional errors when transferring the patient from a medical imaging device in said second chamber to a radiation therapy device in said first chamber, wherein said method of treating the patient comprises the steps of:

a. placing the patient in a treatment position on said table top insert, wherein said table top insert on which the patient is secured is in said cradle of the medical imaging device in said second chamber;

b. generating and marking one or more images of a treatment field on the patient in said treatment position using the medical imaging device;

c. transferring said table top insert from the medical imaging device to the radiation therapy device in said first chamber wherein the patient remains in said treatment position; and d. treating the patient in said treatment position with the radiation therapy device.

33. The improved patient handling system according to claim 1, further comprising a method of treating a patient secured to a table top insert without positional errors when transferring the patient from a medical imaging device in said second chamber to a radiation therapy device in said first chamber, wherein said method of treating the patient comprises the steps of:

a. placing the patient in a treatment position on said table top insert, wherein said table top insert on which the patient is secured is in said cradle of the medical imaging device in said second chamber;

b. generating one or more images of a treatment field and marking said treatment field on the patient in said treatment position with the medical imaging device and a marker and generating one or more radiation isodose representations on said images with a treatment planning computer, wherein said images are on-line treatment portals with superimposed computer generated isodose to the true three dimensional visualized treatment region for radiation therapy.

c. transferring said table top insert from the medical imaging device to the radiation therapy device in said first chamber wherein the patient remains in said treatment position; and d. treating the patient in said treatment position with the radiation therapy device by using conventional and three dimensional conformal radiation therapy, stereotactic radiosurgery and intraoperative radiation therapy.

34. The improved patient handling system according to claim 1, further comprising a method of treating a patient secured to a table top insert without positional errors when transferring the patient from a medical imaging device in said second chamber to a radiation therapy device in said first chamber, wherein said method of treating the patient comprises the steps of:

a. placing the patient in a treatment position on said table top insert, wherein said table top insert on which the patient is secured is in said cradle of the medical imaging device in said second chamber;

b. generating one or more images of a treatment field and its surrounding normal tissue and critical structures in the patient in said treatment position and marking said treatment field on the patient's skin while the patient is in the treatment position with the medical imaging device and generating a radiation isodose with a treatment planning computer, resulting in said images being isodose superimposed port verification images;

c. transferring said table top insert from the medical imaging device to the radiation therapy device in said first chamber wherein the patient remains in said treatment position; and d. treating the patient in said treatment position with the radiation therapy device, thereby maximizing a dose of radiation directed to a tumor in said treatment field and minimizing the dose of radiation directed to the normal tissue and critical structures surrounding the tumor.

35. The improved patient handling system according to claim 34, wherein generating said images with said treatment planning computer results in online medical imaging and improves quality radiation therapy and quality control.

36. The improved patient handling system according to claim 34, wherein generating said images with said treatment planning computer, resulting in online medical imaging, and using said port verification images improves quality radiation therapy and quality control.

37. The improved patient handling system according to claim 1, further comprising a method of treating a patient secured to a table top insert such that there are minimal positional errors when transferring the patient from a medical imaging device in said second chamber to a radiation therapy device in said first chamber, wherein said method of treating the patient comprises the steps of:

a. placing the patient in a treatment position on said table top insert, wherein said table top insert on which the patient is secured is in said cradle of the medical imaging device in said second chamber;

b. generating an image of a treatment site on the patient in said treatment position with the medical imaging device, wherein the medical imaging device is equipped with markers resulting in an image treatment field being marked on the patient's skin and said image is superimposed with radiation isodose distribution to said treatment site and its surrounding normal tissue including the critical structures;

c. transferring said table top insert from the medical imaging device to the radiation therapy device in said first chamber wherein the patient remains in said treatment position; and d. treating the patient in said treatment position with the radiation therapy device, thereby maximizing a dose of radiation directed to a tumor in said treatment field and minimizing the dose of radiation directed to the normal tissue and critical structures surrounding the treatment site.

38. The improved patient handling system according to claim 1, wherein the medical imaging device in said second chamber is used independent of the radiation therapy device in said first chamber such that the medical imaging device is used for routine diagnostic imaging purposes.

39. The improved patient handling system according to claim 1, wherein the radiation therapy device provides advanced radiation therapy such as three dimensional radiation therapy, radiosurgery, intraoperative radiation therapy and three dimensional display of brachytherapy implant source.

40. The improved patient handling system according to claim 1, wherein said radiation shielding means is a rotating cylindrical shielding door having a central opening, a hollow core filled with a radiation blocking material, and a means for rotating.

41. The improved patient handling system according to claim 40, wherein said means for rotating is a motor driven chain.

42. The improved patient handling system according to claim 40, wherein said means for rotating is a mechanical handle.

43. The improved patient handling system according to claim 40, wherein said radiation blocking material is lead.

* * * * *